United States Patent
Barnett et al.

(10) Patent No.: US 9,144,404 B2
(45) Date of Patent: Sep. 29, 2015

(54) MANAGING BODY COMPOSITION

(76) Inventors: John Thomas Barnett, Wollaston, MA (US); Michael R. D'Angelo, Plymouth, MA (US)

(\*) Notice: Subject to any disclaimer, the term of this patent is extended or adjusted under 35 U.S.C. 154(b) by 714 days.

(21) Appl. No.: 13/452,724

(22) Filed: Apr. 20, 2012

(65) Prior Publication Data

US 2012/0215128 A1 Aug. 23, 2012

Related U.S. Application Data

(60) Continuation-in-part of application No. 12/843,511, filed on Jul. 26, 2010, now Pat. No. 8,170,807, which is a division of application No. 11/948,702, filed on Nov. 30, 2007, now Pat. No. 7,788,042.

(51) Int. Cl.
| | |
|---|---|
| *G06F 15/16* | (2006.01) |
| *A61B 5/0488* | (2006.01) |
| *A61B 5/00* | (2006.01) |
| *G06Q 10/10* | (2012.01) |
| *G06Q 50/22* | (2012.01) |

(52) U.S. Cl.
CPC ............ *A61B 5/4869* (2013.01); *A61B 5/0002* (2013.01); *G06Q 10/101* (2013.01); *G06Q 50/22* (2013.01)

(58) Field of Classification Search
CPC ..... A61B 5/0002; A61B 5/4869; G06Q 50/22
USPC .............. 702/19, 20; 600/307, 309, 561, 547, 600/300, 372; 128/879, 898, 903, 920
See application file for complete search history.

(56) References Cited

U.S. PATENT DOCUMENTS

| | | | |
|---|---|---|---|
| 630,643 | A | 8/1899 | Barrie |
| 5,335,667 | A | 8/1994 | Cha et al. |
| 5,372,141 | A | 12/1994 | Gallup et al. |
| 5,783,408 | A | 7/1998 | Hamilton et al. |
| 6,354,996 | B1 | 3/2002 | Drinan et al. |
| 6,539,310 | B2 \* | 3/2003 | Shimomura ............... 702/19 |
| 6,635,015 | B2 \* | 10/2003 | Sagel ..................... 600/300 |
| 7,184,823 | B2 \* | 2/2007 | Ueda et al. ............... 600/547 |
| 7,233,823 | B2 | 6/2007 | Simond et al. |
| 7,399,744 | B2 \* | 7/2008 | Mack et al. ................ 514/4.8 |
| 7,541,547 | B2 | 6/2009 | McGuire et al. |
| 7,788,042 | B2 | 8/2010 | Barnett et al. |
| 8,024,204 | B1 | 9/2011 | Goral |
| 8,170,807 | B2 | 5/2012 | Barnett et al. |

(Continued)

OTHER PUBLICATIONS www.myfooddiary.com, printed from the World Wide Web on Nov. 30, 2007. The examiner should treat this document as prior art for purposes of examining the claims of this patent application (2 pages).

(Continued)

*Primary Examiner* — Carol S Tsai
(74) *Attorney, Agent, or Firm* — Fish & Richardson P.C.

(57) ABSTRACT

Among other things, at least two different independent providers of body composition management services are enabled to have online access through respective graphical user interfaces to body composition information and plans that are associated with respective clients of the providers and that are stored on the server. The graphical user interfaces are different for different independent providers. At least some of the information and plans associated with the clients of the different independent providers are stored in a common format in a common database maintained by the server.

20 Claims, 34 Drawing Sheets

(56) References Cited

U.S. PATENT DOCUMENTS

| | | |
|---|---|---|
| 2002/0022773 A1 | 2/2002 | Drinan et al. |
| 2002/0049546 A1* | 4/2002 | Shimomura .................. 702/19 |
| 2004/0059242 A1* | 3/2004 | Masuo et al. ................ 600/547 |
| 2004/0131227 A1 | 7/2004 | Bravomalo et al. |
| 2004/0131997 A1 | 7/2004 | McGuire et al. |
| 2004/0171464 A1* | 9/2004 | Ashby et al. .................. 482/54 |
| 2004/0243020 A1* | 12/2004 | Ueda et al. .................. 600/547 |
| 2005/0080352 A1 | 4/2005 | Sato |
| 2005/0209528 A1 | 9/2005 | Sato et al. |
| 2005/0240444 A1* | 10/2005 | Wooten et al. .................. 705/3 |
| 2006/0205647 A1 | 9/2006 | Cawthorne et al. |
| 2007/0038092 A1 | 2/2007 | Jean-Claude et al. |
| 2007/0276270 A1 | 11/2007 | Tran |
| 2008/0051679 A1 | 2/2008 | Maljanian |
| 2008/0058610 A1* | 3/2008 | Sato et al. .................. 600/300 |
| 2008/0280922 A1 | 11/2008 | Engelen et al. |
| 2009/0089672 A1* | 4/2009 | Tseng et al. .................. 715/700 |
| 2009/0131814 A1* | 5/2009 | Thompson .................. 600/561 |
| 2009/0143994 A1 | 6/2009 | Barnett et al. |
| 2009/0247897 A1 | 10/2009 | Ashida et al. |
| 2010/0287488 A1 | 11/2010 | Barnett et al. |

OTHER PUBLICATIONS www.weighwatchers.com, printed from the World Wide Web on Nov. 30, 2007. The examiner should treat this document as prior art for purposes of examining the claims of this patent application (1 page).

www.bodybuilding.com/fun/nutrient.htm, printed from the World Wide Web on Nov. 30, 2007. The examiner should treat this document as prior art for purposes of examining the claims of this patent application (3 pages).

http://en.wikipedia.org/wiki/Body_fat_percentage, Nov. 23, 2007 (8 pages).

http://nhlbisupport.com/bmi/, printed from the World Wide Web on Nov. 30, 2007. The examiner should treat this document as prior art for purposes of examining the claims of this patent application (1 page).

http://www.halls.md/body-mass-index/av.htm, May 1, 2004 (2 pages).

Transaction history of U.S. Pat. No. 7,788,042 to Oct. 4, 2012 (1 page).

Transaction history of U.S. Pat. No. 8,170,807 to Oct. 4, 2012 (2 pages).

* cited by examiner

| FIELD |
|---|
| CONTROLKEY |
| VERSION |
| UPDATED |
| NOTE |
| COPYRIGHT |
| TERMSOFUSE |
| LEGALLINK |
| TECHNICALLINK |
| FATFACTORMALE |
| LEANFACTORMALE |
| FATFACTORFEMALE |
| LEANFACTORFEMALE |
| DEFAULTHEADERGRAPHIC |
| DEFAULTFOOTERGRAPHIC |
| DEFAULTBACKGROUNDCOLOR |
| DEFAULTTEXTCOLOR |
| DEFAULTTRAINERKEY |
| DEFAULTFEMALEDENSITYGRADIENT |
| DEFAULTMALEDENSITYGRADIENT |

FIG. 2

| FIELD |
|---|
| ID_USR |
| LEVEL |
| ACTIVE |
| SEED |
| FNAME |
| LNAME |
| NICKNAME |
| BIRTHDAY |
| ADDRESS1 |
| ADDRESS2 |
| CITY |
| STATE |
| ZIP |
| HOME |
| CELL |
| WORK |
| COMMENT |
| PHOTO |
| TRAINERKEY |
| EMAIL |
| PASSWORD_USR |
| PASSWORDHINT |
| HEIGHTINCHES |
| HEIGHTMETERS |
| GENDER |
| BLOODTYPEKEY |
| ETHNICITYKEY |
| FEET |
| INCHES |
| PARTNERKEY |
| ADDED |
| UPDATED |
| ACCEPTEDTERMS |
| TERMSACCEPTEDON |

FIG. 3

| FIELD |
|---|
| NAME |
| PARTNERKEY |
| ADDRESS1 |
| ADDRESS2 |
| CITY |
| STATE |
| ZIP |
| PHONE |
| DESCRIPTION |
| NOTES |
| ADDED |
| UPDATED |
| BACKGROUNDCOLOR |
| TEXTCOLOR |
| HEADERLOGO |
| FOOTERLOGO |

FIG. 4

| FIELD |
|---|
| BCKEY |
| PERSONKEY |
| DATETAKEN |
| WEIGHTLBS |
| WEIGHTKGS |
| ARM |
| CHEST |
| WAIST |
| HIPS |
| THIGH |
| CALF |
| SUBSCAPULARFOLD |
| SUPRAILIACFOLD |
| CHESTFOLD |
| THIGHFOLD |
| ABDOMINALFOLD |
| BICEPFOLD |
| MIDAXILARYFOLD |
| TRICEPFOLD |
| FRONTPHOTO |
| LEFTPHOTO |
| BACKPHOTO |
| RIGHTPHOTO |
| NOTES |

FIG. 5

| FIELD |
|---|
| KEY |
| CLIENTKEY |
| STARTDATE |
| ENDDATE |
| FIRSTBCKEY |
| LASTBCKEY |
| STARTBFP |
| GOALFAT |
| GOALLEAN |
| UPDATED |
| NOTES |
| PROTEINGRAMS |
| CARBGRAMS |
| FATGRAMS |
| CARDIODAYS |
| CARDIOCALORIES |
| STRENGTHDAYS |
| STRENGTHCALORIES |

FIG. 6

| FIELD |
|---|
| LOGKEY |
| PERSONKEY |
| DATE |
| WEIGHT |
| DIETLOG |
| EXERCISELOG |
| JOURNAL |
| SYSTOLIC |
| DIASTOLIC |
| RESTINGHR |
| PHOTO |

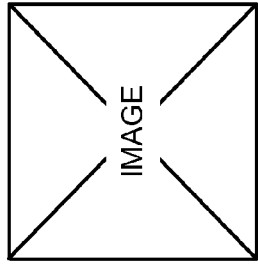
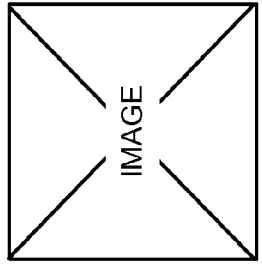
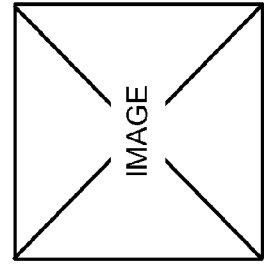
COPYRIGHT NOTICE
USERNAME:
PASSWORD:
LOGIN
FORGOT YOUR PASSWORD?
TERMS OF USE
FIG. 11

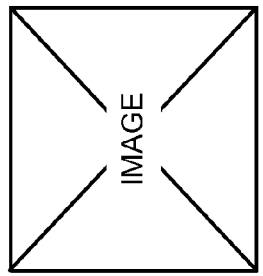
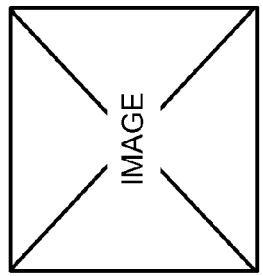
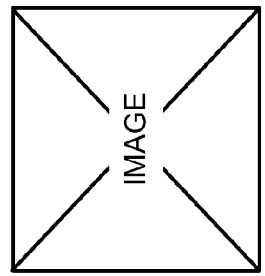
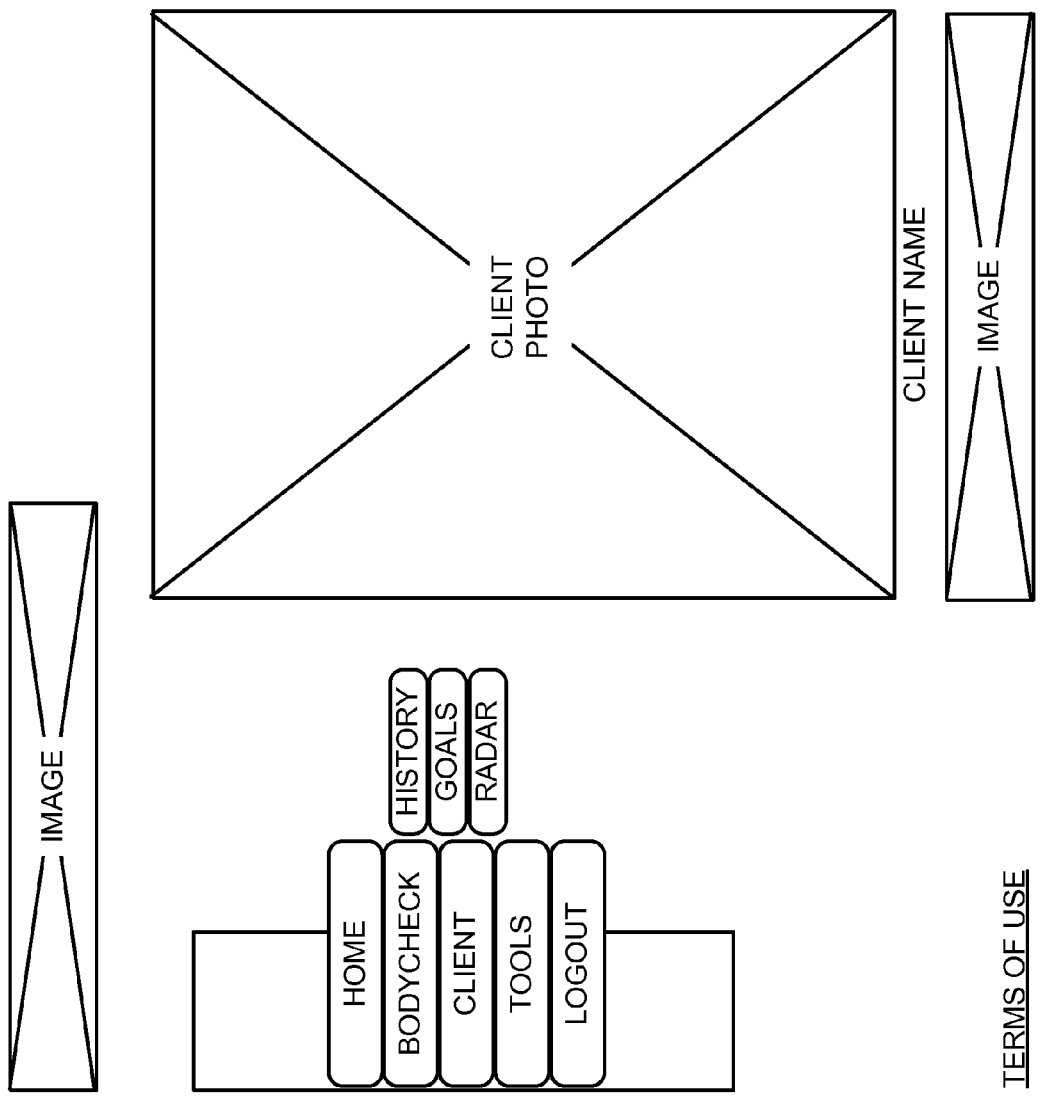
FIG. 15

HISTORY REPORT FOR TEST CLIENT

| TAKEN | WEIGHT | CHEST | CIRCUMFERENCE (IN CENTIMETERS) ||||| 
| | | | ARM | WAIST | HIPS | THIGH | CALF |
|---|---|---|---|---|---|---|---|
| 10/24/06 | 170.5 | 101.0 | 32.5 | 87.0 | 102.0 | 53.9 | 35.4 |
| 11/20/06 | 168.0 | 100.5 | 32.7 | 83.4 | 100.0 | 54.5 | 36.8 |
| 12/19/06 | 168.7 | 101.0 | 33.0 | 83.5 | 99.8 | 53.5 | 37.2 |
| 01/19/06 | 168.5 | 97.5 | 33.5 | 83.5 | 100.4 | 53.5 | 36.8 |
| 03/05/07 | 171.2 | 102.0 | 33.5 | 83.8 | 100.8 | 55.0 | 37.0 |
| 03/22/07 | 168.5 | 100.5 | 33.4 | 82.6 | 99.0 | 54.5 | 36.6 |
| ☒ | ☒ | | | | | | |
| ☒ | | | | | | | |

CIRCUMFERENCE CHARTS

| FIG. 16A | FIG. 16B | FIG. 16C |

| SCAP | TRICEP | BICEP | CHEST | AXILARY | ILLIAC | ABD | THIGH |
|---|---|---|---|---|---|---|---|
| 17.0 | 11.8 | 3.8 | 15 | 18.2 | 39.8 | 48.5 | 12.2 |
| 13.1 | 10.0 | 3.0 | 11.1 | 12.8 | 19.0 | 32.8 | 12.5 |
| 12.2 | 8.4 | 3.0 | 6.2 | 10.3 | 12.5 | 23.8 | 10.8 |
| 11.0 | 8.0 | 3.0 | 7.9 | 8.8 | 10.0 | 23.0 | 10.3 |
| 11.0 | 8.0 | 3.0 | 6.5 | 9.0 | 11.0 | 24.0 | 9.0 |
| 10.5 | 7.9 | 3.0 | 7.9 | 8.2 | 11.0 | 20.8 | 10.0 |

-- SKIN FOLDS (IN MILLIMETERS) --

SKIN FOLD CHARTS

FIG. 16B

| DENSITY | FAT% | -- CALCULATIONS -- | | | |
|---|---|---|---|---|---|
| | | FAT | LEAN | BMR | TOOLS |
| 1.043 | 24.14 | 41.2 | 129.3 | 1,834 | ☒ ☒ |
| 1.056 | 18.47 | 31.0 | 137.0 | 1,943 | ☒ ☒ |
| 1.067 | 14.24 | 24.0 | 144.7 | 2,052 | ☒ ☒ |
| 1.066 | 14.43 | 24.3 | 144.2 | 2,045 | ☒ ☒ |
| 1.067 | 13.96 | 23.9 | 147.3 | 2,089 | ☒ ☒ |
| 1.068 | 13.73 | 23.1 | 145.4 | 2,061 | ☒ ☒ |
| | | CALCULATIONS | | | |

FIG. 16C

| EXPECTED GOAL DATE: | 01/21/08 ▼ |
|---|---|
| BODY FAT: | 6.45% |
| BASE METABOLIC RATE: | 2,056 |
| TOTAL CALORIES STORED AS FAT: | 80,500 |
| TOTAL CALORIC LOSS: | 45,500 |
| WEEKLY LOSS BY DIET: | 1,494 |
| CALORIES BURNED BY EXERCISE: | 2,750 |
| WEEKLY CALORIC LOSS: | 4,244 |
| WEEKLY WEIGHT CHANGE: | -1.21 |
| WEEKS TO GOAL: | 10.7 |

| STRENGTH PLAN | | TOTAL |
|---|---|---|
| DAYS: | ⇕ | 5 |
| CALORIES: | ⇕ | 250 |
| TOTAL: | | 1,250 |

COPYRIGHT NOTICE

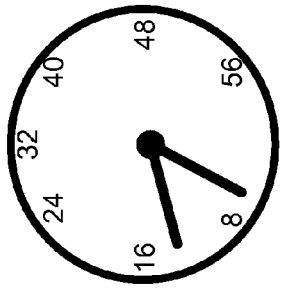

| CARDIO PLAN | | TOTAL |
|---|---|---|
| DAYS: | ⇕ | 5 |
| CALORIES: | ⇕ | 300 |
| TOTAL: | | 1,500 |

FIG. 17

| | CURRENT | GOAL | CHANGE | % |
|---|---|---|---|---|
| ○ FAT: | 23 | ⇕ 10 | -13 | -57% |
| ○ LEAN: | 144 | ⇕ 145 | 1 | .7% |
| ○ TOTAL: | 167 | 155 | -12 | -7.2% |
| BMR: | 2,043 | 2,056 | 13 | .7% |

| | TOTAL | CALORIES | PER LB |
|---|---|---|---|
| PROTEIN: | 220 ⇕ | 880 | 1.5 |
| CARBS: | 144 ⇕ | 576 | 1.0 |
| FAT: | 43 ⇕ | 387 | .3 |
| TOTAL CALORIES | | 1,843 | |
| BMR VARIANCE | | -213 | |

TERMS OF USE

| FIG. 21A | FIG. 21B | FIG. 21C |

FIG. 21

HISTORY REPORT FOR TEST CLIENT

| TAKEN | WEIGHT | CHEST | ARM | CIRCUMFERENCE (IN CM) | | | |
|---|---|---|---|---|---|---|---|
| | | | | WAIST | HIPS | THIGH | CALF |
| 10/24/06 | 170.5 | 101.0 | 32.5 | 87.0 | 102.0 | 53.9 | 35.4 |
| 11/20/06 | 168.0 | 100.5 | 32.7 | 83.4 | 100.0 | 54.5 | 36.8 |
| 12/19/06 | 168.7 | 101.0 | 33.0 | 83.5 | 99.8 | 53.5 | 37.2 |
| 01/19/06 | 168.5 | 97.5 | 33.5 | 83.5 | 100.4 | 53.5 | 36.8 |
| 03/05/07 | 171.2 | 102.0 | 33.5 | 83.8 | 100.8 | 55.0 | 37.0 |
| 03/22/07 | 168.5 | 100.5 | 33.4 | 82.6 | 99.0 | 54.5 | 36.6 |

CIRCUMFERENCE MEASUREMENTS

FIG. 21A

| SCAP | TRICEP | BICEP | CHEST | AXILARY | ILLIAC | ABD | THIGH |
|---|---|---|---|---|---|---|---|
| 17.0 | 11.8 | 3.8 | 15 | 18.2 | 39.8 | 48.5 | 12.2 |
| 13.1 | 10.0 | 3.0 | 11.1 | 12.8 | 19.0 | 32.8 | 12.5 |
| 12.2 | 8.4 | 3.0 | 6.2 | 10.3 | 12.5 | 23.8 | 10.8 |
| 11.0 | 8.0 | 3.0 | 7.9 | 8.8 | 10.0 | 23.0 | 10.3 |
| 11.0 | 8.0 | 3.0 | 6.5 | 9.0 | 11.0 | 24.0 | 9.0 |
| 10.5 | 7.9 | 3.0 | 7.9 | 8.2 | 11.0 | 20.8 | 10.0 |

-- SKIN FOLDS (IN MILLIMETERS) --

SKIN FOLD MEASUREMENTS

FIG. 21B

| -- CALCULATIONS -- | | | | |
|---|---|---|---|---|
| DENSITY | FAT% | FAT | LEAN | BMR |
| 1.043 | 24.14 | 41.2 | 129.3 | 1,834 |
| 1.056 | 18.47 | 31.0 | 137.0 | 1,943 |
| 1.067 | 14.24 | 24.0 | 144.7 | 2,052 |
| 1.066 | 14.43 | 24.3 | 144.2 | 2,045 |
| 1.067 | 13.96 | 23.9 | 147.3 | 2,089 |
| 1.068 | 13.73 | 23.1 | 145.4 | 2,061 |
| CALCULATED VALUES | | | | |

FIG. 21C

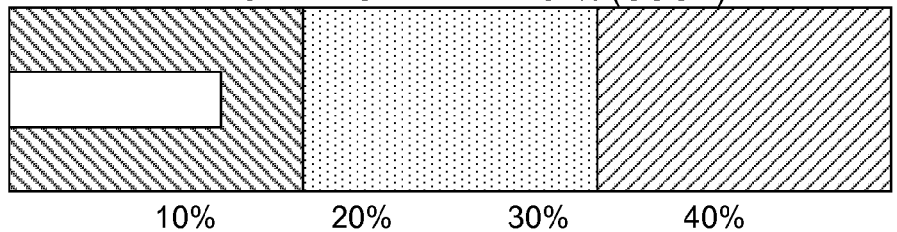
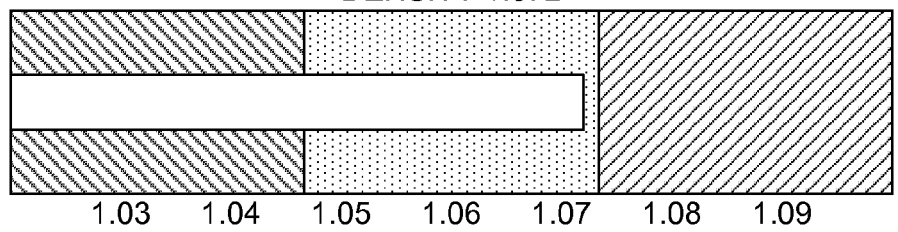
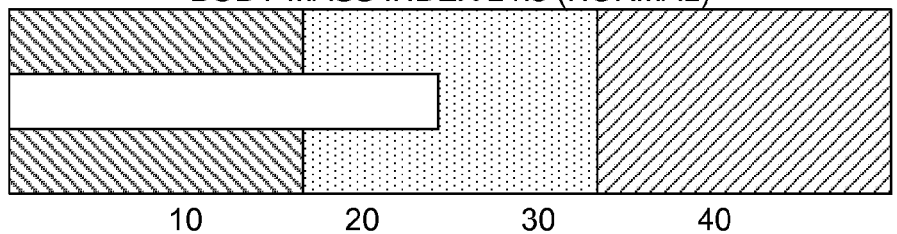
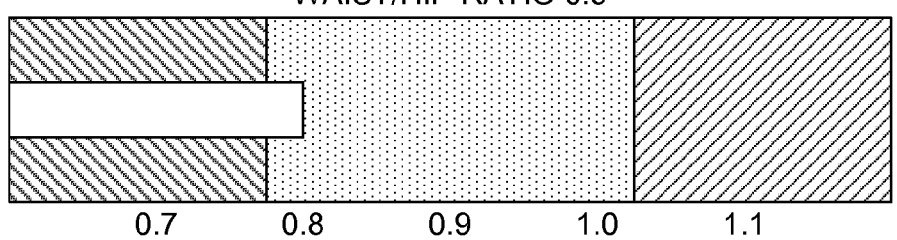
FIG. 23C

MANAGING BODY COMPOSITION

CLAIM OF PRIORITY

This application is a continuation-in-part and claims priority under 35 U.S.C. §120 to U.S. patent application Ser. No. 12/843,511, filed Jul. 26, 2010, now U.S. Pat. No. 8,170,807 now allowed, which in turn is a divisional of and claims priority under 35 U.S.C. §120 to U.S. patent application Ser. No. 11/948,702, filed Nov. 30, 2007, and issued as U.S. Pat. No. 7,788,042 on Aug. 31, 2010. The entire contents of all referenced applications are hereby incorporated by reference.

This description relates to managing body composition.

Body composition generally refers to how much fat, bone, internal organ tissue, and muscle make up a person's body. The lean body mass (LBM) (bone, internal organ tissue, and muscle) and fat body mass (FBM) in a person's body depend significantly on three major factors: genetic predisposition, what food and how much of it the person eats, and the extent to which the person exercises or is generally active.

Body composition may affect a person's health and appearance. Strength and stamina, for example, depend on a foundation of well-developed and/or conditioned lean body mass. A person who is fat (that is, who has a high percentage of fat body mass) is thought to be at higher risk of disease and systemic health problems. On the other hand, it is essential for good health to have a minimum percentage of fat body mass.

The overall base metabolic rate (BMR) of a person (which affects how easily the person can "burn" the calories that he consumes) depends upon the total weight of the person's lean body mass. Lean body mass has a higher metabolic rate than fat body mass for a given body weight. Given a certain amount of lean body mass in a person's body, a person with more fat body mass may tend to consume relatively more calories than his body is able to burn than would a person having the same lean body mass and less fat body mass. The excess calories consumed by the fatter person are stored as additional fat, which can degrade the person's health.

People in certain cultures, and those who understand and monitor how their bodies work, pay close attention to their body compositions and follow casual or strict dietary and exercise training programs aimed at reaching and maintaining (e.g., managing) a desirable body composition. Sometimes people rely on others, including trainers, dieticians, and health practitioners to help them manage their body compositions.

Effective management of body composition over a period of time depends on having good metrics for aspects of body composition. The metrics should be reasonably easy to measure or calculate and should represent aspects of body composition that are important to the strength, stamina, appearance, and health goals of the individual who uses them.

A classic metric is the relationship between a person's weight and height compared to other people of the same gender. Although easy to measure, the person's weight alone gives essentially no information about the proportions of lean body mass and fat body mass that make up the body. Height is also easy to measure, and the weight and height of a person, when considered together with percentage of body fat, may give clues about the relationship of lean body mass to fat body mass.

Another metric, body mass index (BMI) relates weight to height by a simple mathematical formula that yields a value on a scale that is used to classify the general fatness or thinness of a person within broad statistical norms in the general population, which change significantly over long periods of time. Ranges of BMI values are sometimes associated with corresponding degrees of healthiness.

Another commonly used metric is the percentage of fat mass in a person's body. While historically difficult to measure accurately, there are now many techniques for determining fat mass percentage accurately and there are medically accepted standards that associate ranges of the value with degrees of physical training and health.

Trainers, dieticians, and others (for example, health practitioners) who help people to follow programs to manage their body compositions typically perform measurements of one or more of the metrics at the beginning of the program, set targets for the metrics to be achieved, and make regular measurements during the course of the program to gauge progress in reaching the targets. How accurately and regularly the measurements are taken, and how effectively information about how they relate to the person's health, strength, and stamina are described, displayed, and understood, have much to do with how effectively the program progresses toward the targets. In some cases, computer programs and online systems can be used to record and track metrics against goals.

SUMMARY

In general, in an aspect, at least two different independent providers of body composition management services are enabled to have online access through respective graphical user interfaces to body composition information and plans that are associated with respective clients of the providers and that are stored on the server. The graphical user interfaces are different for different independent providers. At least some of the information and plans associated with the clients of the different independent providers are stored in a common format in a common database maintained by the server.

Implementations may include one or more of the following features. The providers include trainers and entities that employ trainers. The graphical user interfaces include common elements and private label elements.

In general, in an aspect, a value of maximum fat mass is determined that represents an amount of fat mass that an individual should not exceed for good health. The value of maximum fat mass is determined as a function of height and gender based on a body of statistical data across a population. A value of minimum lean mass is determined that represents an amount of lean mass that the individual should not fall below for good health, the value of minimum lean mass being determined as a function of height and gender based on a body of statistical data across a population. The individual or a trainer of the individual is enabled to manage body composition of the individual based on the determined values of the maximum fat mass and the minimum lean mass.

Implementations may include one or more of the following features. The enabling includes displaying information associated with the determined maximum fat mass and minimum lean mass and measured fat mass and lean mass of the individual to the individual or trainer. A lean mass ratio and a fat mass ratio are determined from respectively the minimum lean mass value and a measured lean mass, and the maximum fat mass value and a measured fat mass. The lean mass ratio and the fat mass ratio are provided to the individual or the trainer for use in connection with management of body composition of the individual.

In general, in an aspect, demographic, health status, and lean mass, fat mass, and other physical data about individuals are received, statistical analyses of the received data are performed to establish demographic lean mass and fat mass values, and the values are made available to individuals and parties who provide services to individuals in connection with managing body composition, without disclosing the identities or private information of any of the individuals about whom the data was received.

Implementations may include the following feature. The physical data is received from the individuals or parties who provide services to the individuals.

In general, in an aspect, a target body composition management value is derived for a person from the person's height, weight, body mass composition, and statistical physical information about a comparable population of individuals. The target body composition management value is provided for use in managing the person's body composition.

Implementations may include one or more of the following features. The target body composition management value includes a body mass index (BMI) value. The target body composition management value includes a version of a conventional BMI value that is adjusted based on body composition data. The conventional BMI value is adjusted upwardly in proportion to a value based on lean body mass and downwardly in proportion to a value based on fat body mass. Information about the target body composition management value is displayed to the client or a trainer. The information includes the conventional BMI value and an adjusted BMI value. The information includes graphical elements illustrating an effect of fat body mass or lean body mass or both on an appropriate BMI value.

In general, in an aspect, a target value associated with a targeted fat mass and lean mass body composition of a person to be achieved by a future date is generated. A slope is displayed that begins at a starting point associated with a starting date and ends at an ending point associated with the future date, the starting point representing a starting value and is based on measurements on the starting date. A trajectory is displayed that traverses mid-points having values that are based on measurements on dates between the starting date and the ending date.

Implementations may include one or more of the following features. The target value is associated with weight. The target value is associated with a component of body mass. The component of body mass includes fat mass or lean mass. The target value is associated with a ratio for a component of body mass. The ratio includes fat mass ratio or lean mass ratio. The slope includes a straight line. The slope and the trajectory are displayed at the same time. The slope and the trajectory are associated with a goal session for the person.

These and other aspects and features, and combinations of them may be expressed as methods, systems, apparatus, combinations, program products, and means for performing functions, and in other ways.

Other advantages and features will become apparent from the following description and from the claims.

DESCRIPTION

FIG. 1 is a block diagram.
FIGS. 2 through 7 are portions of a database schema.
FIGS. 8 through 20 are line drawing representations of screen shots.
FIG. 21 is a table.
FIG. 22 is a graph.
FIGS. 23A, 23B, and 23C are a report.
FIGS. 24, 25, 26, and 27 are graphs.
FIG. 28 is a BMI diagram.

For good health, strength, and stamina, a person's body should have at least a certain minimum lean mass (MLM) and a certain maximum fat mass (MFM). Having more lean mass than the minimum is generally good as is having no more than the maximum fat mass. The desirable minimum lean mass and maximum fat mass can be determined for a person and set as goals for a body composition management program. In order to track a person's performance against those goals, the actual lean body mass and the actual fat body mass can be measured, by various methods, at the beginning of the program and regularly during the program. By storing and making available information about progress with respect to the minimum lean mass and maximum fat mass and other metrics, the person's dietary and training efforts can be sharply focused on the metrics that matter, and success of the program is more likely.

As shown in FIG. 1, in some implementations of the system described here, a body composition management system 10 provides online body composition management services and information to (and receives, accumulates, and analyzes information received from) one or more trainers 12, 14, 16 . . . 18, one or more partners 22 . . . 24, and one or more individual clients 28 . . . 32 to aid them in effectively managing the body compositions of the clients. In these examples, managing body composition can include, for example, accepting registrations by the partners, the trainers, and the clients, receiving and storing data and measurements about each of the clients, one or more times, receiving and storing information about body composition goals of the clients, storing the measured values and goal information over time, and reporting the information to the clients, the trainers, and the partners.

The body composition management services may be provided from one or more servers or other computers and from one or more other stationary or portable electronic devices 34, 36, 38 . . . 40 that are located with a client, with a trainer, with a partner, or at a central location 48. The body composition management services may be provided using an application program 50, 52 that may be running in association with a central web server 55 that delivers the services through a network 57 such as the Internet, or as a standalone application running in a location associated with a partner, a trainer, or a client. In some implementations, the services can be provided by a cooperative operation of applications running at a server and a local facility.

All or portions of the information required to operate the system are stored, maintained, and accessed in a database 54, 56 . . . 36, that can be located only at the server or only at local facilities or can be distributed at a number of different locations.

The clients who are served by the system 10 are individuals who seek to manage their body compositions for good health, good appearance, stamina, and/or strength. The number of clients served by the system could range from only a few to hundreds, thousands, or even millions. They could be located in cities or rural areas anywhere in the world. They may or may not be associated with trainers and partners.

We use the term trainer to refer to any individual who is an exercise or strength trainer, a dietician, a health professional, or other individual who helps clients, directly or indirectly, to manage one or more aspects of their body compositions and to reach goals associated with body composition management. The number of trainers involved in the system could range from only a few to dozens or thousands or more. Each trainer is associated with at least one client and as many as dozens or hundreds of clients. Each client is typically associated with one or a small number of trainers.

A partner is any kind of enterprise, for example, health care providers, and underwriters or a gym or a weight clinic, that provides, one or more body composition management services directly to one or more clients (or indirectly to clients through one or more trainers). Each partner can be associated with one or more trainers and with one or more clients or any combination of them. Each trainer and each client can be associated with one or more partners. We sometimes refer to partners and trainers as providers. In some cases an individual trainer can operate as a partner.

The system shown in FIG. 1 can be replicated by one or more other similar systems and the systems can be interconnected or independently operated. Different systems can be operated in different geographic areas or by different partners or groups of partners, or by groups of trainers, or even by groups of clients. Different systems can maintain independent databases or can cooperate in the maintenance of joint databases.

Some of the database information about clients is personal, for example, their names and other identifiers, and other database information (including metrics and calculated values associated with body composition and goals) is treated as anonymous, such as the height, weight, lean body mass, fat body mass, BMI, BMR, percentage of body fat, and others described later, that is, it is not tagged with any personal identifiers. The effective use of some of the metrics and calculated values in the database depends on statistical information accumulated and analyzed across a larger population, for example, data that associates percentage of body fat with health conditions. The data based on statistical information can be developed internally by the system, can be shared among systems, or can be received from an outside source 60. Conversely, anonymous data in the database that is useful as part of larger bodies of data about broader populations can also be shared among databases and provided to an external user of such data 60. By such sharing of anonymous data the effectiveness of the body composition management programs conducted using the system can be improved.

In some implementations, a system uses a single central web server associated with an application and a central database to provide services for body composition management through the World Wide Web to computers and portable and handheld devices that are controlled by a variety of partners, a variety of trainers, and a variety of clients, who can have a range of relationships with one another.

In general, the system described here enables, among other things, (1) goals to be established, maintained, and adjusted over time for each client for raw and calculated metrics associated with body composition, good health, strength, and stamina, (2) a succession of measurements of the client over time with respect to the raw metrics to be acquired, stored, maintained, and accessed as needed by the client, her trainers, and her partners (with appropriate controls to protect privacy), (3) other metrics to be calculated, stored, maintained, and accessed from the raw metrics, (4) performance of the client against the goals to be calculated, displayed, stored, maintained, and accessed as needed, and (5) information to be accessed, displayed, understood, and used interactively through a simple, convenient user interface.

The system can make use of conventional metrics, including BMI, BMR, RMR (Resting Metabolic Rate) body fat percentage, weight, height, and others. In addition, the system uses special metrics that are effective in managing body composition for good health, strength, and stamina.

For this purpose, the system represents the relationship between actual body masses (LBM and FBM) and desirable body masses in two ratios: a minimum lean mass ratio (MLMR) and a maximum fat mass ratio (MFMR). The minimum lean mass ratio is the ratio of the actual lean mass of a person to a desirable minimum healthy lean mass (MLM) for the person. The maximum fat mass ratio is the ratio of the actual fat mass to a desirable maximum fat mass (MFM) for a person. Positive values of MLMR indicate more than the minimal needed lean body mass and are considered good. Negative values of MLMR are considered bad. Positive values of MFMR are considered bad (because the person has more than the desirable maximum amount of fat) and negative values are considered good, except that a very low value of MFMR may indicate a potential health risk.

We define a desirable body composition factor (BCF) that mathematically defines, based upon an analysis of statistical data across a population, the MFM and MLM for a person of a specific gender and height. Based on an example population that was analyzed for this purpose, the formula for MLM and MFM for male and female subjects as a function of height is:

For males:

$$\text{MFM(pounds)} = \text{round}(((\text{height in meters}/5.1423822805848300)*\text{height in inches}),0)$$

$$\text{MLM(pounds)} = \text{round}(((\text{height in meters}/0.9795013867780630)*\text{height in inches}),0)$$

in which 0 is the argument to the "round" function and indicates that the rounding is to zero places, that is, an even number of pounds.

For females:

$$\text{MFM(pounds)} = \text{round}(((\text{height in meters}/3.29112465957429)*\text{height in inches}),0)$$

$$\text{MLM(pounds)} = \text{round}(((\text{height in meters}/1.09704155319143)*\text{height in inches}),0)$$

For a person whose lean mass and fat mass match the desirable MFM and MLM values, the ratios MLMR and MFMR are both unity.

The BCF formulas may be updated and refined as more data from the general population becomes available and can be analyzed statistically. For this purpose anonymous data in the databases may be shared and analyzed.

The database can be in the form of a relational database that includes a number of tables. Some implementations of the database can include the following tables for that purpose.

Other implementations could have databases and tables arranged in a wide range of ways, and can include more or less information than the examples described here.

A table called "control" organizes system configuration parameters including, for example, as shown in FIG. 2, the version, the date updated, notes, a copyright notice, and current MFM and MLM values for males and females, which have been derived by statistical analysis.

A table called "people" contains one record for each person (e.g., client) who is enrolled, for example, as shown in FIG. 3. The table contains specific identifying and demographic data related to the individual that generally does not vary. The record also contains certain fixed measurements of the person that relate to body composition (or values calculated from the measurements), such as an initial body weight and a final fat mass. A key id_usr points to other tables that contain variable data about the person, such as regular information accumulated during body checks, activity and nutrition logs, and a daily journal. Also recorded in the "people" table is a logical indication that the terms of use (recorded in the "control" table) have been accepted and the date when the terms were accepted. Acceptance of the terms is required for enrollment. If the required terms change re-acceptance can be mandated.

The table "partners", for example, as shown in FIG. 4, contains one record for each partner of the system. Records in the partners table can be nested to document corporate relationships among partners. A partner record contains pointers to graphical items used in the "private label" interface of the web pages that will be served to trainers and clients who are users of that partner's services. This allows a common shared interface to be customized to reflect the brand of the partner, for example, "Bill's Gym". The partner record also contains data for the base font, font color, font size, and background and foreground colors. The record is indexed using a unique system generated key value (partnerkey), which connects the record to the client record that is selected either during an individual's login or from a customized list of people provided to an authorized partner.

A table called "skins" is associated with the partners table and is used, for example, to maintain information necessary to establish the graphic elements of the user interface. Recording interface elements in the "skins" table allows multiple interface styles or "skins" to be developed for each partner. These skins can be displayed programmatically for example, based upon time of year, client, trainer, or partner preference, or other factors.

A table called "bodycomp" (see FIG. 5) contains one record for each body check of a person, including all raw numeric metrics collected during the body check. In some implementations, values that are computed from these metrics and other data on-the-fly by the application at the time of display are presented through the user interface. This allows new or adjusted mathematical algorithms to be applied easily to the data as the algorithms are developed. In other implementations, some or all of the computed values can be stored in the database and recalculated from time to time. Each bodycomp record contains enough data to describe accurately the physical state of the person at the time of collection. Compelling and statistically significant data may be obtained by analysis of the anonymous data contained in these and other similar records.

Comparisons and analyses of the data may be made based upon any of the metrics recorded or calculated. Trend data may be developed over time. The data contained in each bodycomp record allows on-line calculation and reporting of statistical information relevant to an individual. For example, a 46 year-old man could ask for and view a scatter plot graph of his MLMR (in a unique color) compared to the MLMRs of all 46 year-old men recorded in the system or in a broad group of similar systems. In a text-based report, the value can be reported as a variation from the mean, standard deviation, or other statistical measure. The system may be enhanced by correlating current client body composition values with potential health risks. For example, morbidly obese persons are at an increased risk for heart disease and diabetes.

The system can accept body fat percentage values (BFP) from a variety of sources, for example, by calculation from skinfold and circumference measurements, from bio-electric-impedance (BEI), hydrostatic weighing, X-Ray and CAT scan analysis Skinfold measurement is the most accurate of the easily applied techniques.

For each client, one or more goal sessions can be defined and tracked. A goal session, for example, includes a starting date and an ending date and goal values for one or more raw or calculated metrics that are to be reached at the ending date. A table called "goals" (FIG. 6) contains one record for each goal set (e.g., a body composition management program) established by or for a client. A client can have one or more than one goal session, for example, a succession of goal sessions one after the other, or alternative goal sessions that overlap in time.

For example, as shown in FIG. 6, a goal session contains start and end dates, starting body fat percentage (BFP) and ending fat body mass and lean body mass values. Using relationships with other tables, one or many body checks recorded at the beginning of and during the period of a goal session may be selected and displayed. The delta values between the starting and ending (goal) fat body masses and lean body masses allow expectation slopes (sometimes called glide slopes) to be developed and tracked during the course of the goal session. The values recorded in body checks during the course of the session, when plotted against the expectation slopes, provide feedback about the person's progress toward the goals. The ending date and goals may be adjusted as needed. Nutrition and exercise components of the goal may be adjusted to match the person's actual performance and therefore better match the expectation slopes to the person's capability. A wide variety of other raw and calculated metrics can form the bases of the goal sessions, the expectation slopes, and the body checks. In some implementations, other tables can also be maintained for reference purposes, among others. For example, an "activity" table (not shown) captures descriptions of human activities and the equivalent metabolic values. A "daily log" (FIG. 7) includes records each of which captures an instance of information entered by a person concerning daily values such as weight, periods of exercise, or a photograph. Each record of a "foods" table (not shown) associates food with details about its nutritional content and value.

A table called "charts" contains one record for each chart type displayed by the system. In concept, the table divides the chart into three standard code blocks: header; body; and footer. These blocks contain the program code required to generate custom graphic objects based upon numeric data contained in other tables or produced by programmatic computation. The fourth element of the program code is gender specific and is recorded in the appropriately named gendermale and genderfemale columns of the table. Data in the table are referenced by chartname and relationships are maintained with the system managed primary index (chartkey).

In other implementations a wide variety of other raw and derived data and the results of analyses of data also can be stored and made available.

Examples of how the web-based user interface could be implemented for a partner that is serving trainers and clients are illustrated by the web pages shown in the figures and described as follows. A wide variety of other interfaces would be possible, including interfaces suitable for small hand held or portable devices. A wide variety of types of information and functionalities can be provided in the interface. FIGS. 8 through 23 are provided as line drawing versions of full color or gray-scale images of screen shots to comply with patent office rules. The line drawing versions do not illustrate all of the color, shading, layout and other graphical aspects of the screen shots. Copies of versions of the full color or gray-scale images from which the line drawings were prepared are being submitted as an Appendix to this application and are incorporated here by reference in their entirety. The applicant reserves the right to import any or all features shown in the Appendix figures into the formal figures in this application, including the color features.

As shown in FIG. 8, an initial screen seen by a user (generally, when we refer to user we mean a person who is interacting with the user interface, which could be a client, a representative of a partner, or a trainer, depending on the context) bears graphical elements defined in the database for the partner on behalf of which the user interface is being served. The graphical elements include a logo, colors, page background, font sizes and colors, and a greeting. The initial page includes two simple buttons. One button is invoked to join the system that is offered by the partner represented by the current instance of the user interface. The other button is used by a registered party (a trainer or a client) to login.

Figure 9:
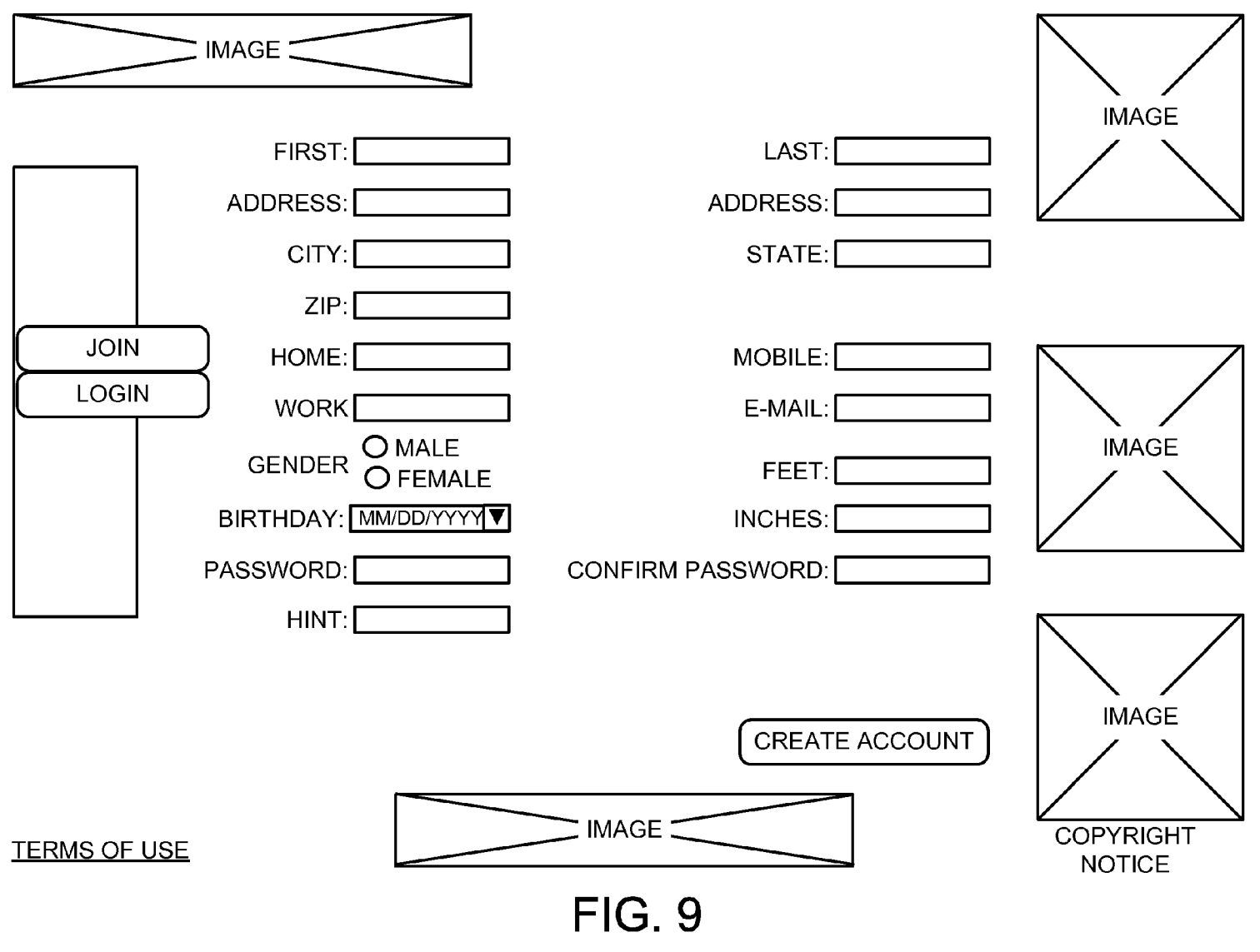

FIG. 9 shows the join screen that permits a new client to create a profile by providing items of identification and contact information, set a password, and enter basic physical information. Clicking the button labeled Create Account causes a new record to be created in the people table of the database.

FIG. 11 shows an example of a typical login page, which requires the user name (typically the person's email address) and the user's password.

Figure 1:
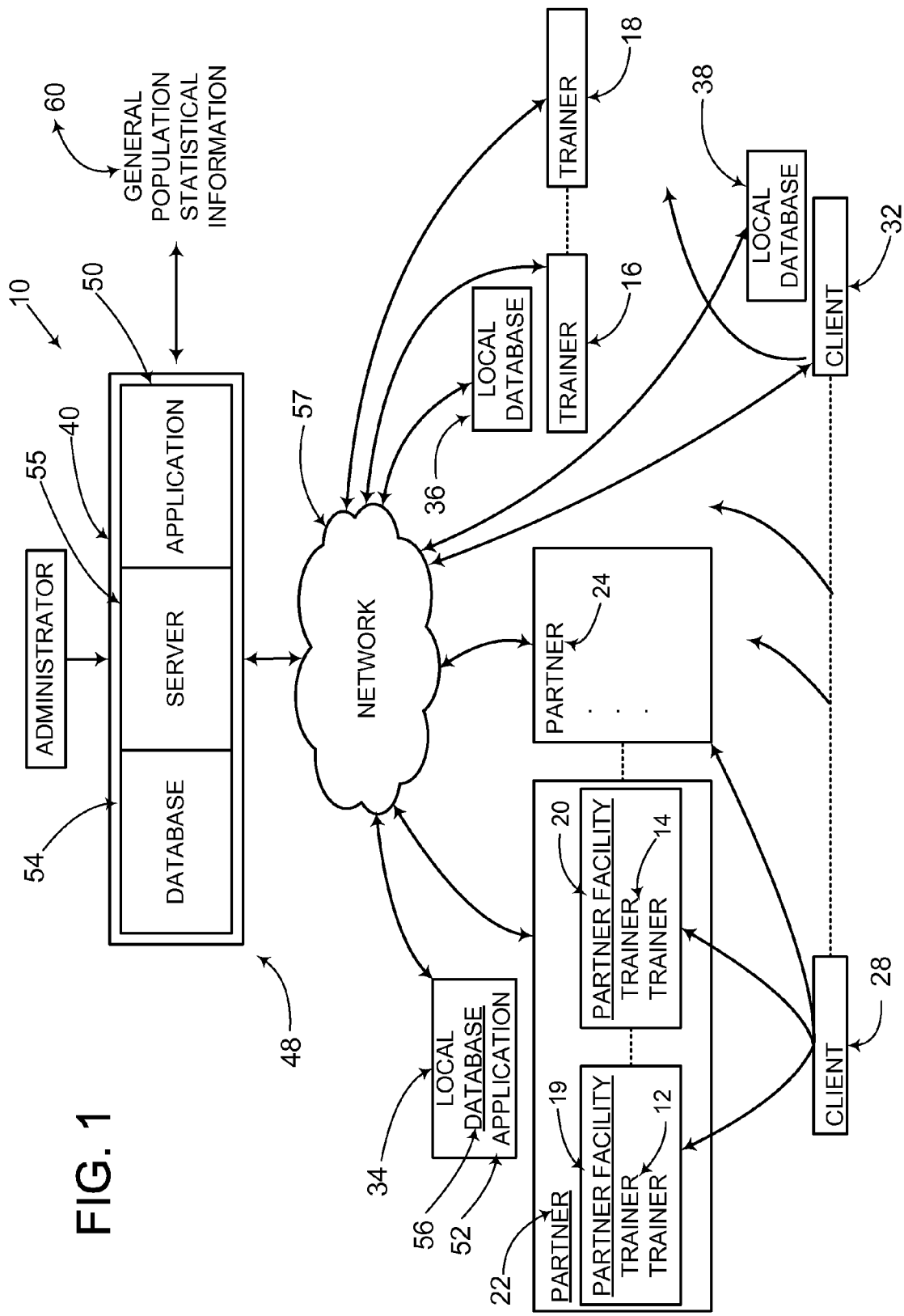
Figure 8:
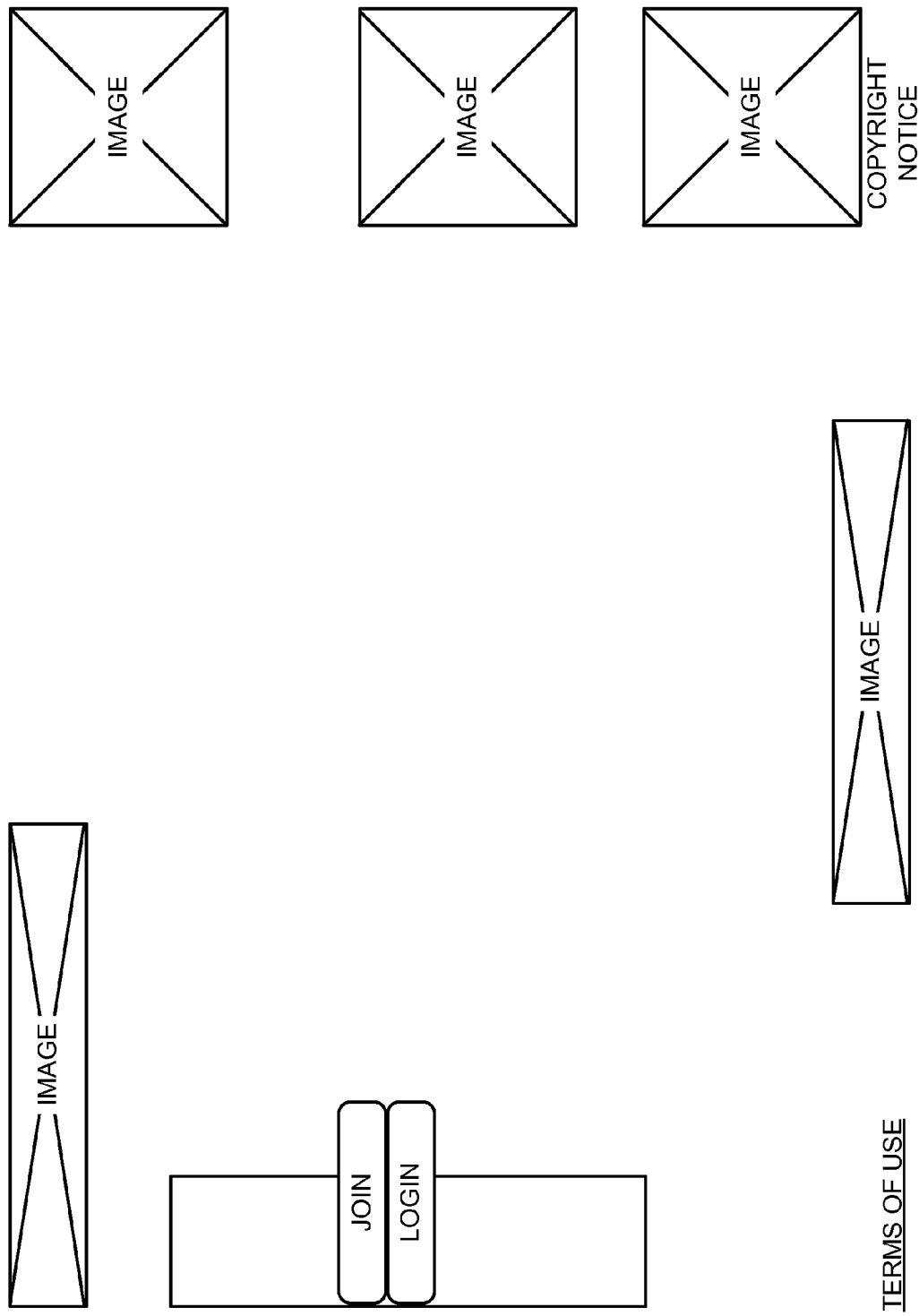
Figure 10:
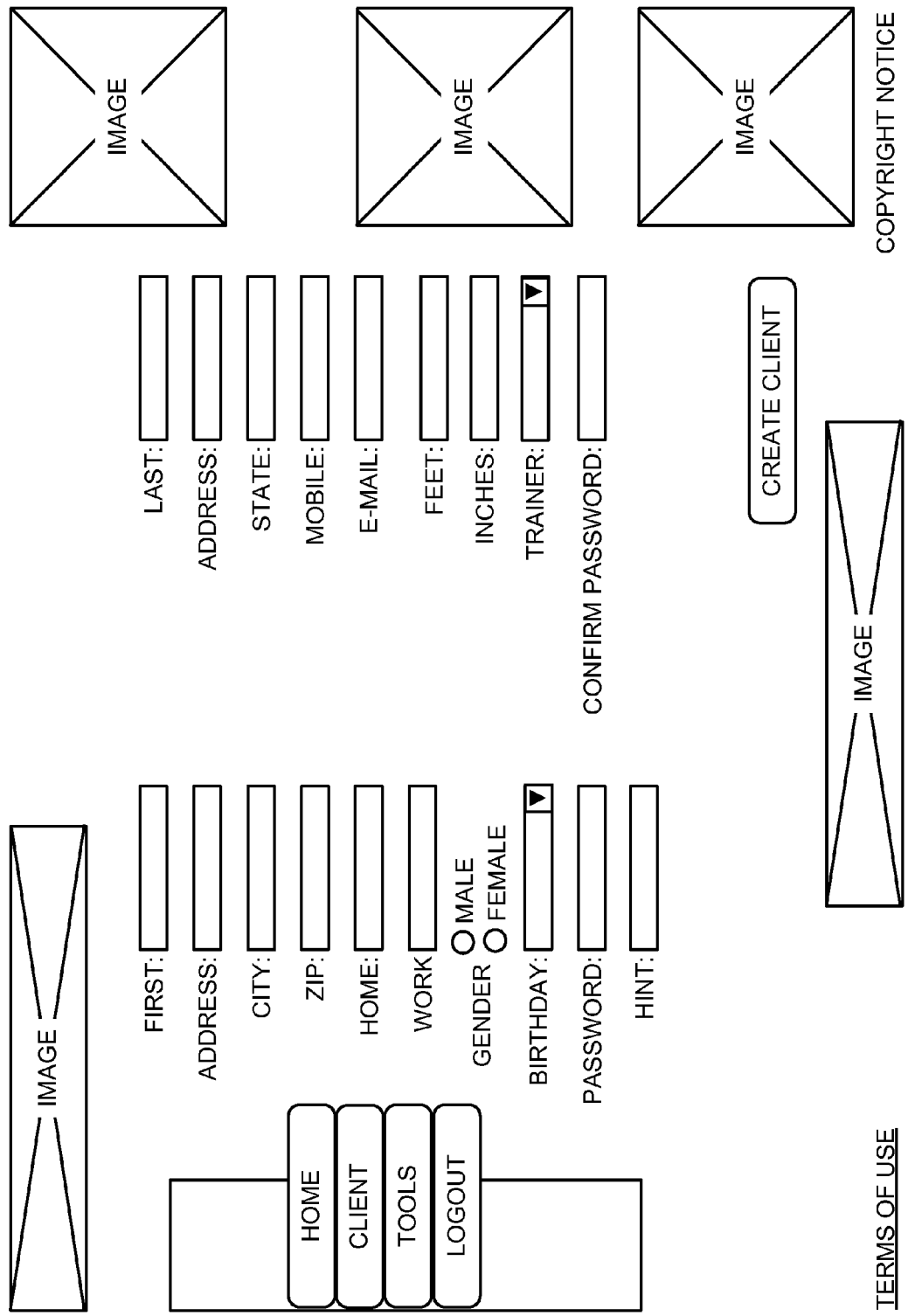
FIG. 10 is a similar screen that enables a trainer to create an account for a new client of the trainer. When the Create Client button is clicked, a new record is created in the people table of the database.
Figure 12:
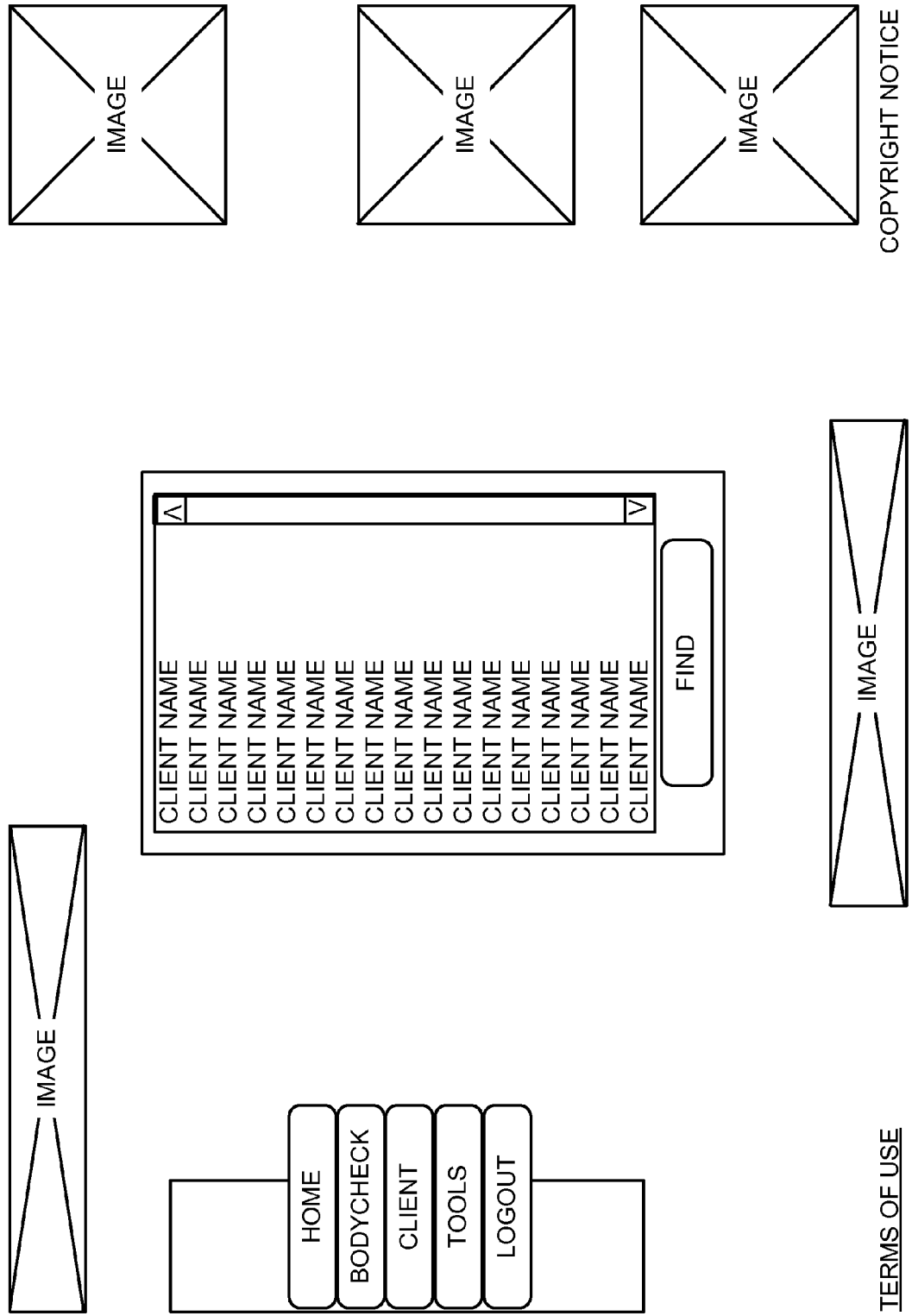

If the user who logs in is a trainer or an administrator or representative of a partner, the screen shown in FIG. 12 appears. In the center, a scrollable list of clients contains the names of people who have joined and are therefore in the database and who are associated with that partner or that trainer (and other clients will not be shown). The trainer (we sometimes use the word trainer as including an administrator or a partner) can then select a client whose information is to be viewed. A navigation bar on the left of the screen has five buttons that enable the user to return to the home screen, enter measurements and other data associated with a body check, view information about the client, participate in a forum, or logout.

Figure 13:
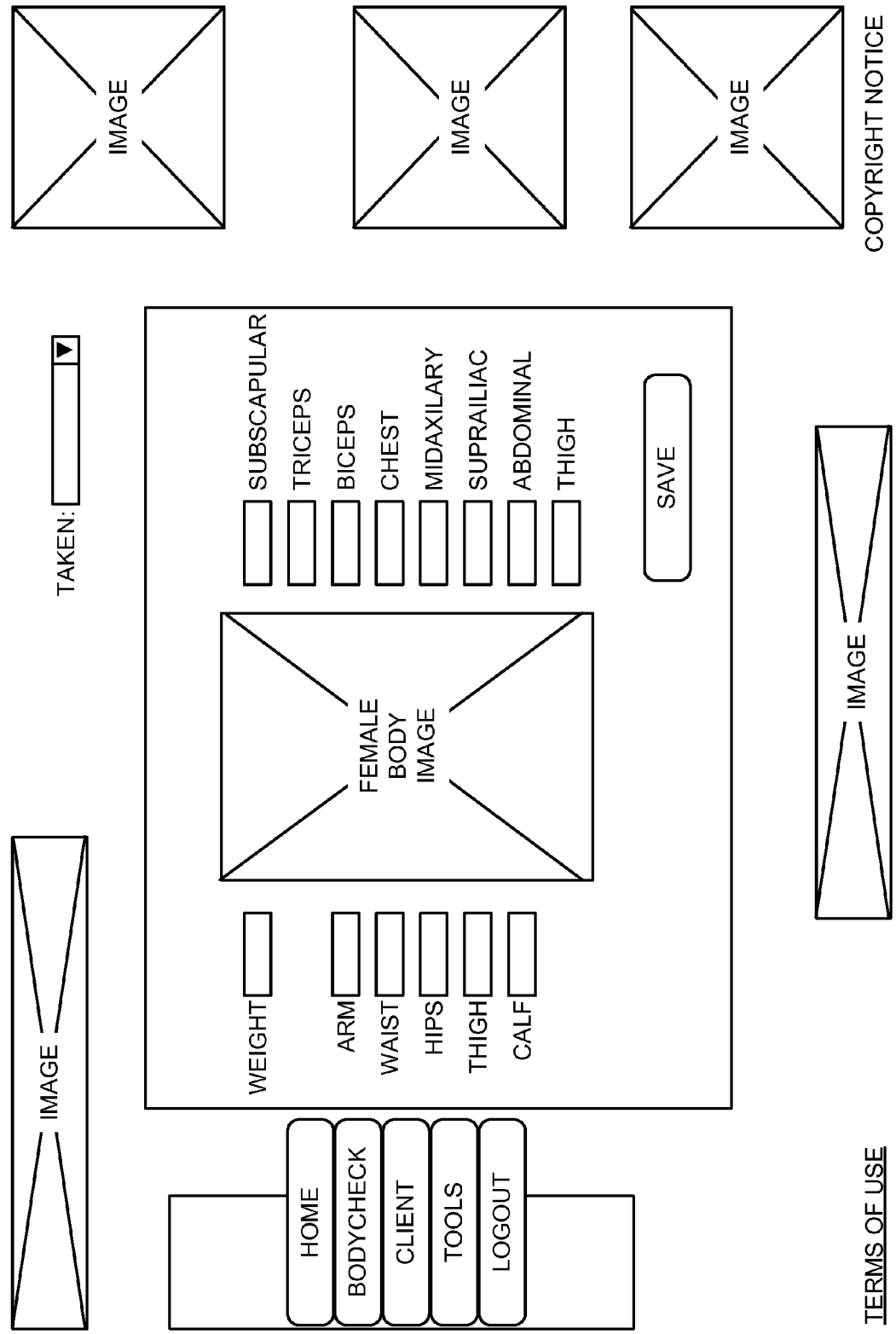
Figure 14:
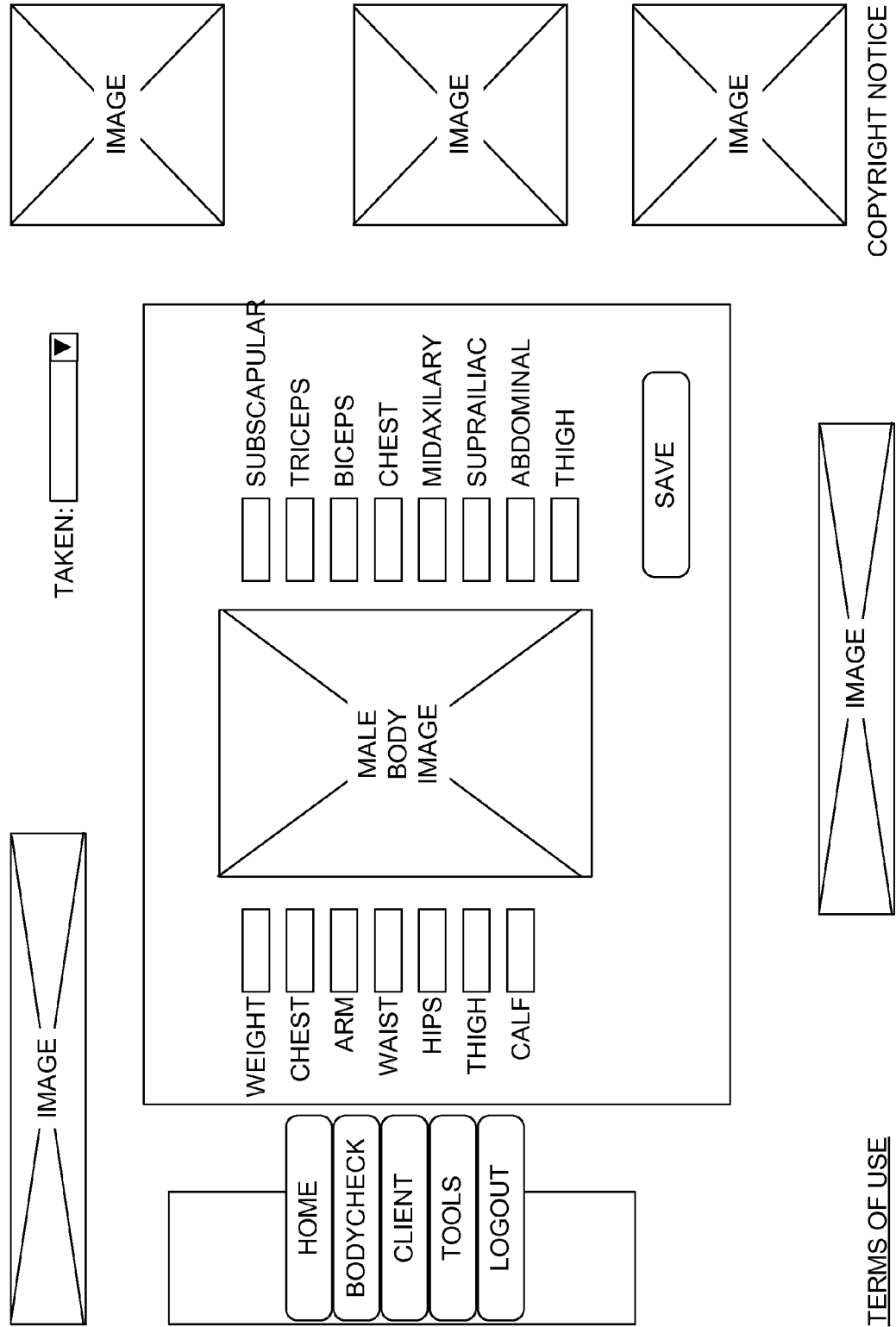

The screen for entering the date and results of body check measurements is shown in FIG. 13 for a woman and in FIG. 14 for a man. When the Save button is clicked, the entered information is stored in the bodycomp table of the database.

If the user who has logged in is a trainer and has selected a client and clicked the client button (or if the user herself has logged in) then the screen shown in FIG. 15 will appear. The screen includes a photograph of the client from the database, if one is available, and the client's name. The client button on the left navigation bar has spawned sub-buttons that enable the user to select to see a history of the client's participation in the body composition management program, the goals set by the client, or the radar display of the client's progress.

Figures 16, 16A:
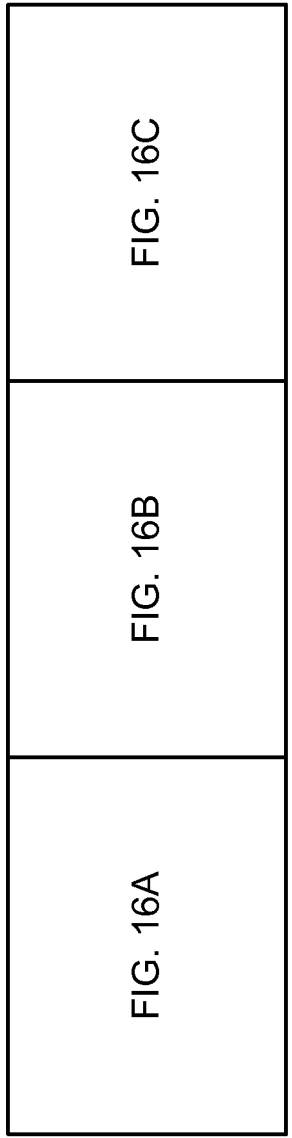

FIG. 16 shows a screen containing a history report that is invoked when the history sub-button of FIG. 16 is clicked. The information in the table of FIG. 5 is drawn from the body check database records for the client. The table provides information and access to other screens that relate to body checks for this client.

Each line of the table contains data from a record of the body check table, including the date, measurements taken on that date, and calculated values. Links on the right end of each row permit the user to navigate to notes and photographs associated with the body check. A link on the left end of each row leads to the full related body check report. The links along the top of the table are each associated with a chart over time of the indicated metric. Groups of charts can be invoked using the links along the bottom of the table. The links at the lower left of the chart enable the user to print the history report, create a new body check record or edit an existing one.

When the goals sub-button on FIG. 15 is invoked, the screen shown in FIG. 17 is displayed. The client's goals of a goal session, plans for meeting those goals, and an illustration of how performing according to the plan will affect progress toward the goals are provided in FIG. 17.

The goals page shown in FIG. 17 is a core instant feedback mechanism of the system. Upon completion of an initial body check, the goal tracking system extracts current body composition information and uses this data as a starting point of the current goal program. The BCF values for the client's actual MLM and MFM are computed when the application is initialized. The values are computed using the core formulas recited earlier based on the client's gender and height. These values are used to populate roll-over icons which provide guidance for the goal setting process. Initially the goal tracking system presents the current lean and fat weights and computes macro nutrition values derived from the base metabolic rate of the client.

The interface allows the client or the trainer to increase or decrease the goals for fat body mass and lean body mass to establish new fat and lean weights. The end date when the goals are expected to be accomplished can be selected from a graphical control. Upon selection, the system calculates the number of days in the goal session from the start date and the end date. Numeric values may be adjusted for macro nutritional elements (protein, carbohydrates, and fat). As these values are updated, the caloric values are computed and the impact is computed against the BMR determined from the current BodyCheck record. The impact of cardiovascular exercise is added to the plan by adjusting the number of days on which cardio exercise is performed, and the number of calories expended per day of cardio vascular exercise.

The system can accurately factor in the caloric impact of other activities (yoga, palates, rollerblading, for example). This capability is based upon the BMR multiplied by the metabolic equivalency (met) value contained in the activity table. Thus, if a person has a BMR of 2,400 calories per day (100 calories per hour) and engages in vigorous rope jumping (12 met) for 1 hour, she will have expended 1200 (12×100) calories. This accurate caloric calculation is an example of customization to the individual characteristics of the client. In a similar manner, the impact of resistance training is incorporated into the plan as values representing the number of days in which the client engages in resistance training and the number of calories expended per day. Each modification to fat mass or lean mass; dietary intake; cardiovascular expenditure; or exercise expenditure is immediately reflected in the cumulative impact section of the display. This allows the client or trainer to immediately understand the impact of any change made in the goal program. When changes are complete, the settings are recorded for future analysis. The system will not allow a client or trainer to set a goal which is not realistically attainable. Additionally the system alerts when goal values may have negative health impact.

The table in the upper left corner shows the client's body composition goals and current metrics, including the client's current fat mass, lean mass, and total mass in the first column, the goal for those metrics in the second column (these can be adjusted using the adjustment buttons), and the change (in the third column as a value and in the fourth column as a percentage) from the current values to the goals that are implied by the first two columns. The bottom row shows the calories that correspond to the current base metabolic rate (BMR) which is inferred by computation from the current fat body mass and lean body mass values, and from the goal mass values. Base metabolic rate is a gender neutral value that may be computed as round(((1.3*(leanmass (in pounds)/2.2))*24),0), which yields the approximate number of calories which are required by the client to exist in a resting state without gaining or losing weight. Calories necessary for walking about, food digestion, and exercise are in addition to this amount. The basic diet recommendations are obtained by the following formulas, which represent the minimum nutrition values required to support a client's individual lean body mass. For males, Protein calories=LBM*1.1; Carbohydrate calories=LBM*1.0; Fat calories=LBM*0.3. For females, Protein calories=LBM*1.0; Carbohydrate calories=LBM*0.8; Fat calories=LBM*0.3. These values may be represented as percentages or adjusted as required by the individual performance of the selected client.

The table in the lower left illustrates a planned diet mix for caloric intake combining protein, carbohydrate, and fat. The first column sets forth the amount of each in grams and permits adjustment of the goals. The second column shows the conversion of grams to calories, and the third column shows the number of grams per pound of the client's weight. The total number of calories is compared to the calculated number of calories that correspond to the BMR for the client, and the calculated variance is shown in the bottom row. A negative variance represents a shortfall of calories compared to BMR which would translate into the body using stored calories to make up the deficit (and conversely).

The table in the middle of the bottom of FIG. 17 captures one possible view of the client's cardio plan, that is the plan for vigorous cardio-vascular exercise that tends to burn calories. The number of days per week in which cardio exercise would be done (five in the example shown) is adjustable. The expenditure of calories for each of the exercise days would be 300 (an adjustable number) in this example, yielding a calculated total expenditure of 1,500 calories per week. While this is the direct impact of cardiovascular exercise the system may also include recovery factors including, but not limited to EPOC (Exercise Post Oxygen Consumption). As statistical research improves, values may change or be added. Depending upon the client's preference, or device type used, the displayed parameters may be summarized or expanded.

In the lower right is a strength training plan that sets an adjustable goal for the number of lifting days per week and a number of calories expended in each day, with the calculated total appearing in the bottom row. The strength training plan relates to exercise intended to build lean body mass.

In the upper right, the system displays to the user information that implies how much progress the client is expected to make toward the goals per week during the goal session. The displayed values include the measured percentage of body fat, the calculated BMR in calories, and the calculated calories stored as fat. The calculated total caloric deficit represents the number of calories of fat body mass that must be lost in order to reach the goal amount of fat body mass. The next three lines show the deficits that would be attributable to reducing food calories, to exercise (including cardio and weight), and to the total of those two values. The deficit values are recalculated in real time as goal values are changed by the user in the various tables. In the example, the total deficit is 4,244 calories which corresponds to a calculated weight change per week of 1.21 pounds.

Figure 18:
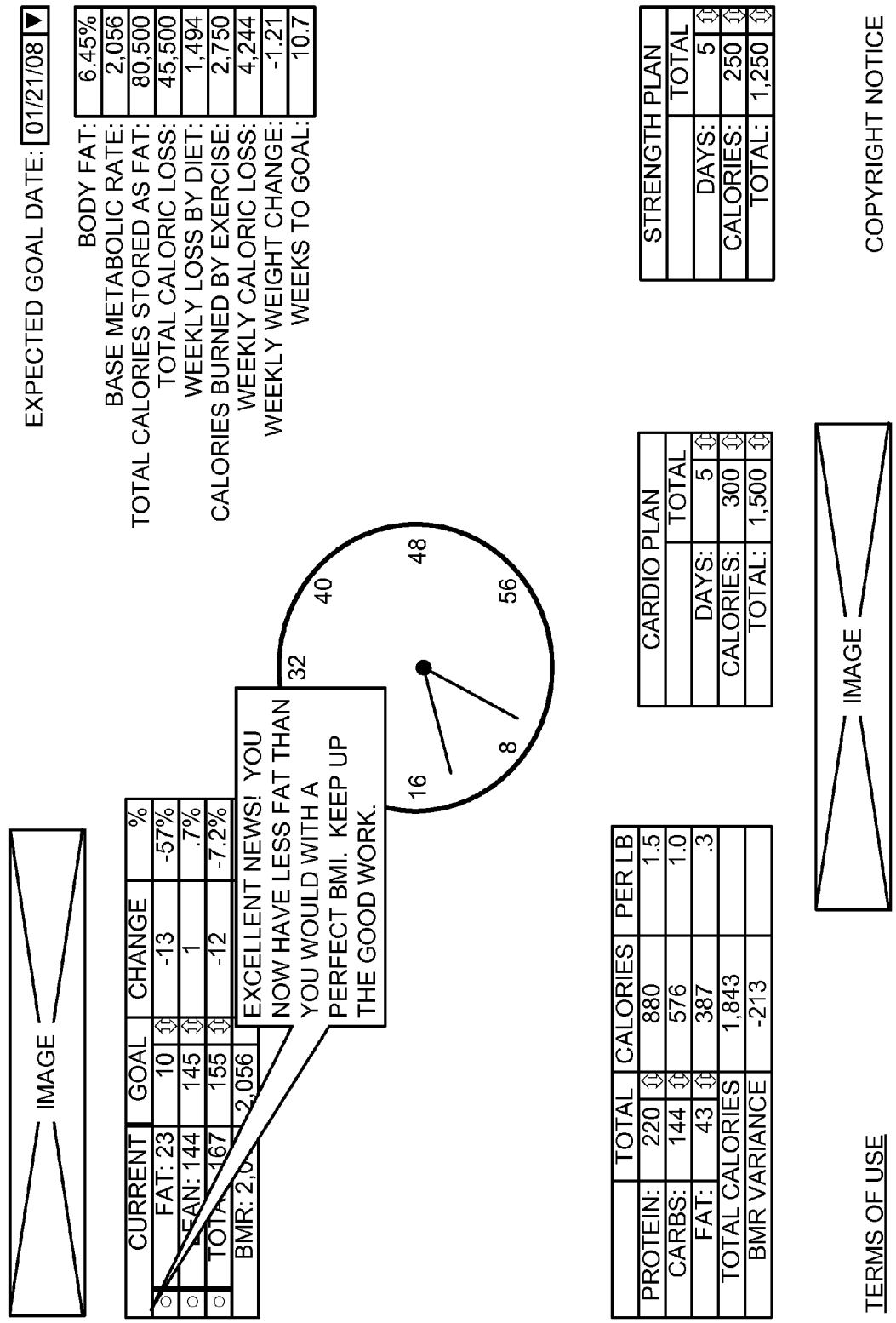

This weight reduction is to be achieved not only by reducing the calories eaten, but also by cardio exercise and strength training. The client's goals in the upper left table include no loss of lean body mass. The strength training plan is designed to assure the maintenance of lean body mass as the total weight of the client is reduced. This is achieved by calculating the protein needed to meet the requirements of the lean mass using a grams per pound calculation. The result is adjusted using judgment based on the mid-point readings taken during the course of the goal session. These readings allow the client's current body composition to be compared with the body composition expected at any mid-point date in the goal session. With these readings, quick adjustments may be made to diet and exercise plans. The client may also be taught that as fat is lost from the body some percentage of it will be lost from inter-muscle tissue. This will increase the overall quality of the muscle, but may result in a minimal loss of lean mass. It is also possible to calculate, report, and manage the quality of muscle (lean body mass). Measurements may be done using electromyography (EMG), which reports the electrical activity of a muscle under contraction. The values rise with the strength (quality) of the contraction. When a client is properly instrumented (electrical leads attached to the muscle group being studied), values may be recorded for specific muscle groups and exercises. Over time, the values recorded while the muscle is under contraction will increase. The ratio of change between earlier and later readings may be used to compute a lean mass ratio LMR quality factor. For example an initial reading obtained while the pectoral muscle is under contraction may be 200.38 microvolts. A later reading might be 210.34 microvolts. This results in a ratio of 1.0497. The ratios may be graphed to show variation over time. Various methods exist for the measurement of muscle contraction including, for example, tension, and velocity. Studies may also be performed to measure the quality and quantity of fast and slow twitch muscle fibers and their respective contractions; these values can be used in the measurement of strength and stamina of the client's lean body mass. Other methods for determining muscle quality may be included. Returning to the table in the upper left of FIG. 17, at the left end of each row is a dot the color of which provides more information in response to a rollover of the mouse cursor, for example, as shown in FIG. 18. A dot also can be colored (red-bad, yellow-caution, green-good) to provide visual feedback regarding the values being set. Other graphic elements, such as a dumbbell, a light bulb, and a starburst, could also be used.

The performance dial in the upper center of FIG. 17 uses a circular analog dial and dial pointers to indicate progress against goal. In the example shown, a goal for percentage body fat is indicated by a green needle. An actual current percentage of body fat is shown by a red needle. Other needles could be used for other raw and calculated metrics.

The goal numbers set by the user can be saved and recalled using the save goal and recall goal buttons.

Figure 19:
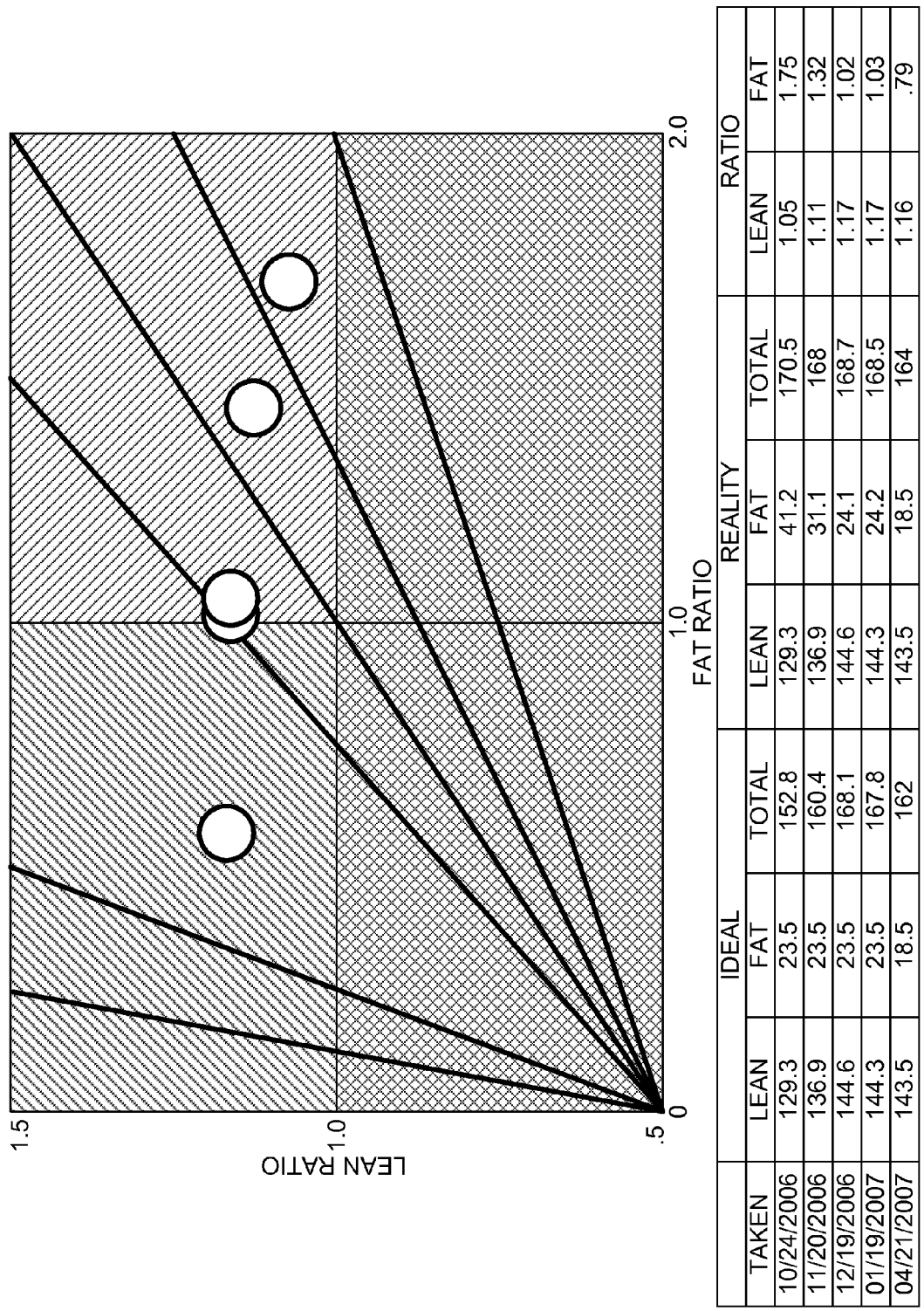

When a user invokes the Radar sub-button on the navigation bar of FIG. 15, he may be shown a radar plot, for example, the plot shown in FIG. 19. The y-axis of the plot represents the MLMR and the x-axis the MFMR. The center point of the plot represents a locus in which both ratios have the value of 1, that is, the ratios of the minimal lean body mass and maximum fat body mass to the goal values are both 1. The scale of values along each axis can expand or contract depending on the location of the values to be plotted. For example, for a fat person, the scale for MFMR could have a right end that is higher than 4. The center point represents a desirable state for the client's fat mass ratio and lean mass ratio. The optimum state of those values for a given client may vary from the center point depending on his or her personal goals or requirements. For example, the optimum fat mass ratio may be substantially below b 1.0.

Dots on the plot can indicate the two ratios at different times. Although not shown in color on the figure, an example is shown in FIG. 19. The initial value may be shown in red, the most recent value in gold, and an intermediate value in blue. The color and size may also be adjusted to emphasize other elements, such as dangerously low body fat. Plotted points that are closer to the upper left of the radar plot indicate excess lean body mass (compared to the minimum desirable) and reduced fat body mass (compared to the maximum desirable), which are both positive indicators. Conversely, points that are closer to the lower right indicate unfavorable values. The radar plot uses two different graphical features to inform the viewer. Again, although the figure reproduced here does not show color, background colors of yellow and orange may be used to imply increased health risk and of red to imply definite health risk. A background color of green may imply favorable conditions. In addition, pie-shaped segments of the plot are defined by rays that project from the lower left corner. Points that lie within a given segment represent roughly similar body composition conditions. Thus, it would typically be useful to engage in a training program that results in moving generally from the lower right toward the upper left across segment boundaries rather than to move from one point to another point within a given segment.

The table shown below the plot contains key values from the body check history. Each row represents a body check.

Figure 20:
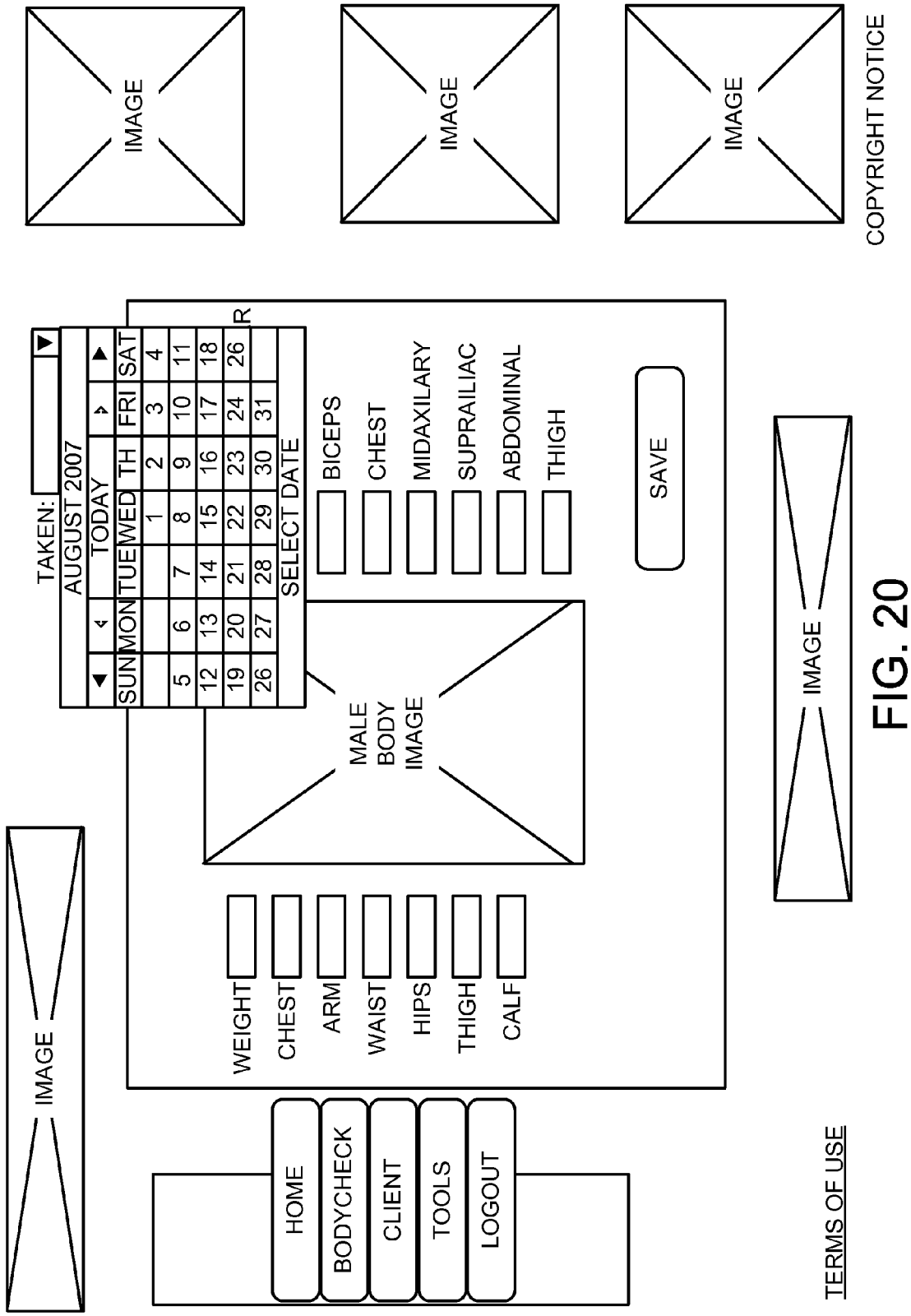

When the body check button on FIG. 12 is clicked, the screen shown in FIG. 20 may be presented to the user. This screen presents the main data entry form for body check data. The entered data is used to populate a record of the database.

Figure 22:
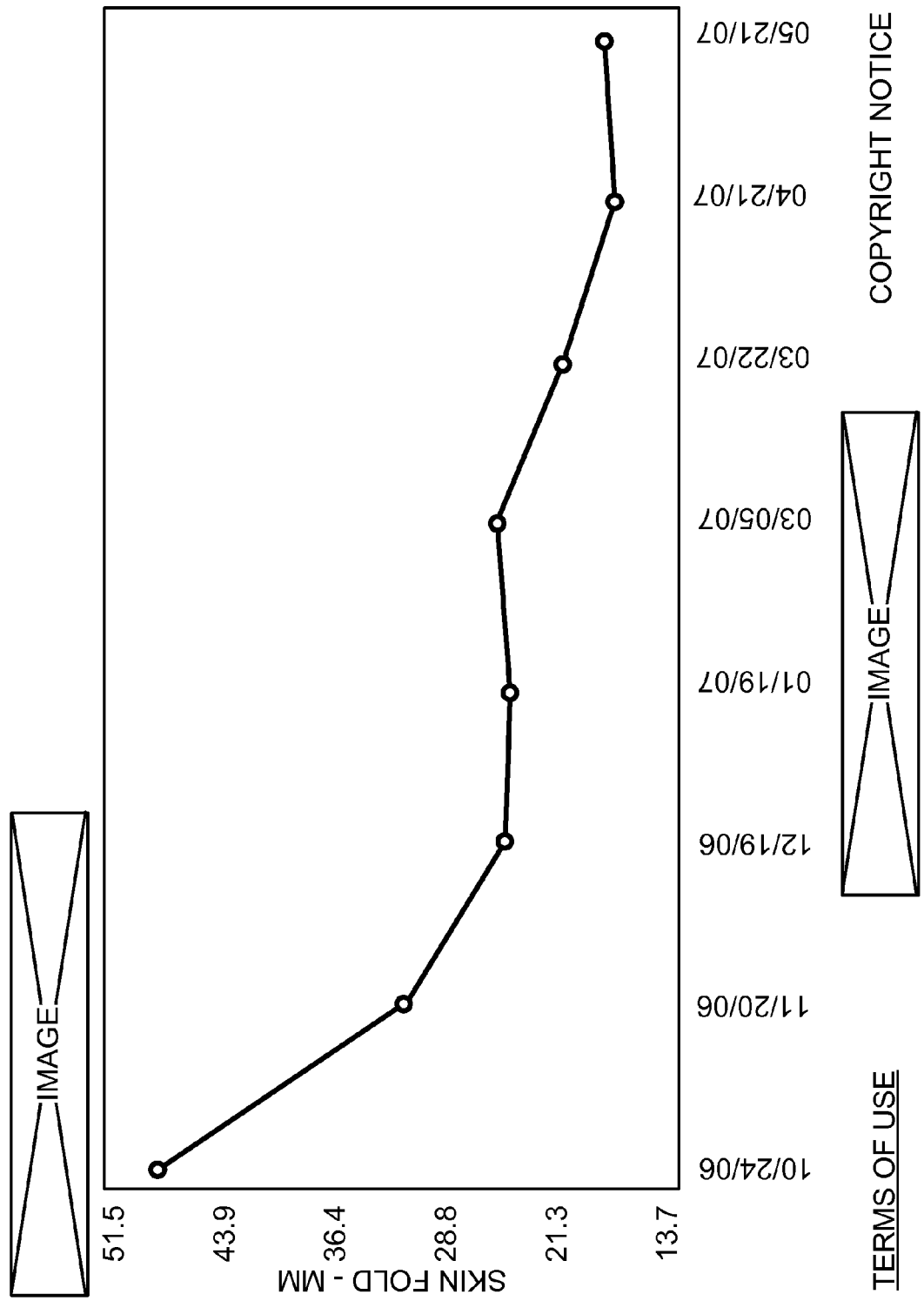

When the user invokes one of the columns in the body check history table (which is shown larger in FIG. 21), a chart is displayed. An example is shown in FIG. 22, which tracks abdominal skin fold values over time based on the dates when the body checks were made. The charts of the kind shown in FIG. 22 may be generated using FusionCharts (available from InfoSoft Global (P) Ltd., located in India) or other graphing technology (e.g., HTML-5). The links that are available in the table of FIG. 16 allow immediate drill down to charts like the one shown in FIG. 22 and thus provide immediate quantifiable and personal feedback to the client about his or her physical state, history, and history of measured performance.

Figure 23:
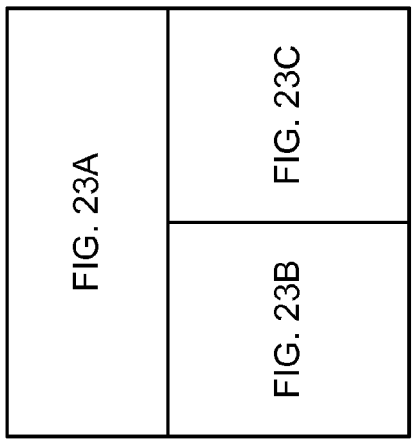
Figure 23A:
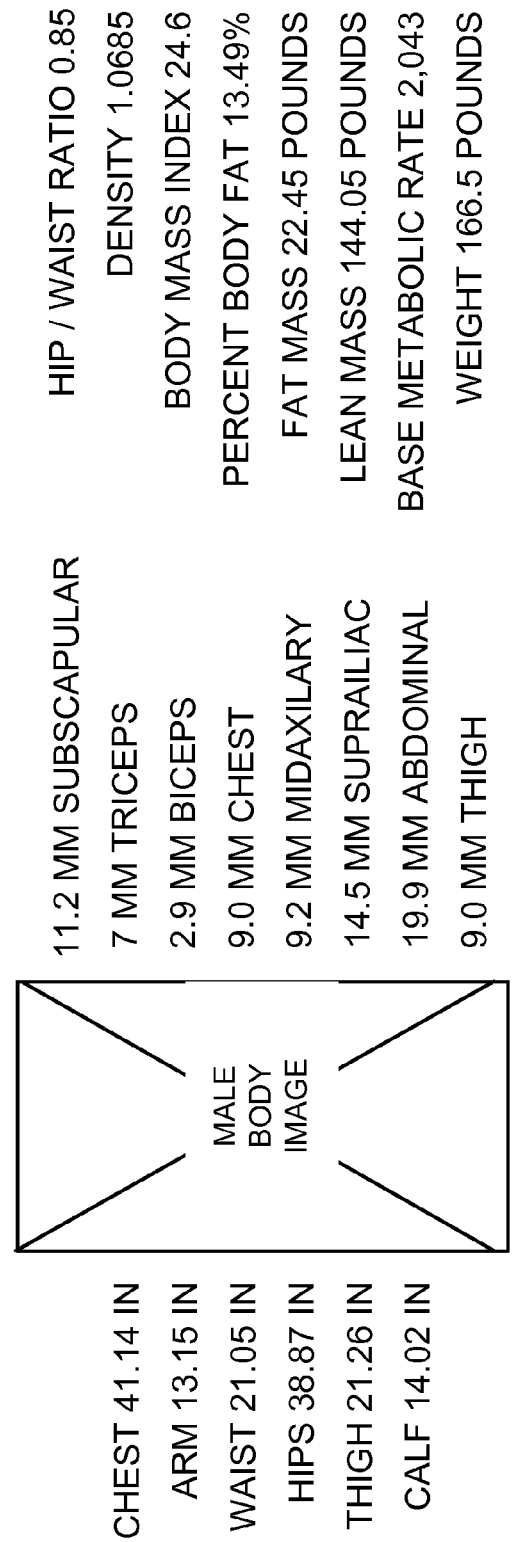
Figure 23B:
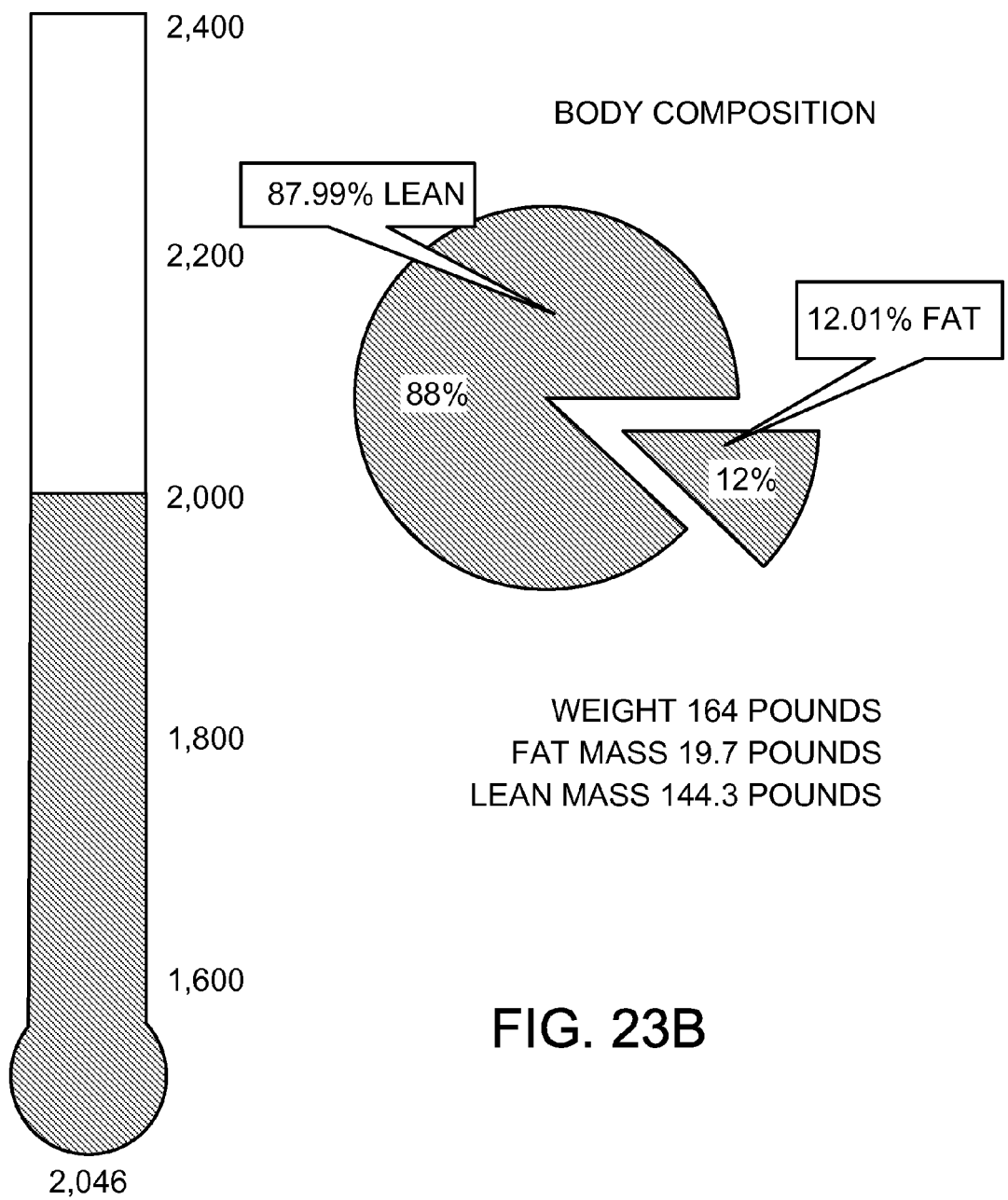

For a given body check, the metrics accumulated and values calculated from the metrics can be shown to a user in graphical form, for example, as shown in FIGS. 23A, 23B, and 23C.

The database associates historical and current data about an individual client with the client's name or other identifier, in order to enable the trainer, partner, or client to use the data for personal and individual purposes. In addition, the information in the database may be accumulated and reported in a manner that disassociates the current and historical data from the personal identification information. The database is structured to permit simple queries of a kind that gather or accumulate individual values and statistical data that is anonymous. For example, a query could obtain the mean body fat percentage for males between the ages of 40 and 50. In a central server a database can be maintained that is anonymous or non-anonymous. Data can be kept anonymous by permitting identifying information to be accessed only when a correct combination of user name and password yield a unique person key (id_usr). Only with this key can identifying information be unlocked from the database. However, statistical queries can be run against the bodycomp table which contains no user identifiable information apart from a link back to the people table. When system maintained queries, are used identifiable information is not revealed. Passwords are required for administrator access and these are controlled and changed on a regular basis.

In some implementations, the database and the calculation engine may be arranged, for example, so that only raw measured values or user entered data are stored persistently while calculated values are not stored but are calculated only as needed. In this way, if measured values or entered data needs to be corrected, the calculated values do not have to be recalculated until they are needed. In addition, the database can store a broader range of raw values and entered data that is used at a given time for calculations. By storing the measured values in raw form, when refinements are made later to the formulas for calculating derived values from possibly a different or more comprehensive set of raw values, the values are easily available in the database. Among other things, this will permit the derived values to be customized based on gender, ethnicity, age, body type (ectomorph, mesomorph, endomorph), or extreme value of fat mass or lean mass.

The use of roll-over dots throughout the user interface provides simple and quick information to a user concerning good (green), caution (yellow), and bad (red) values to be considered. When the mouse cursor is rolled over a dot additional detailed information about the condition becomes available.

Figure 24:
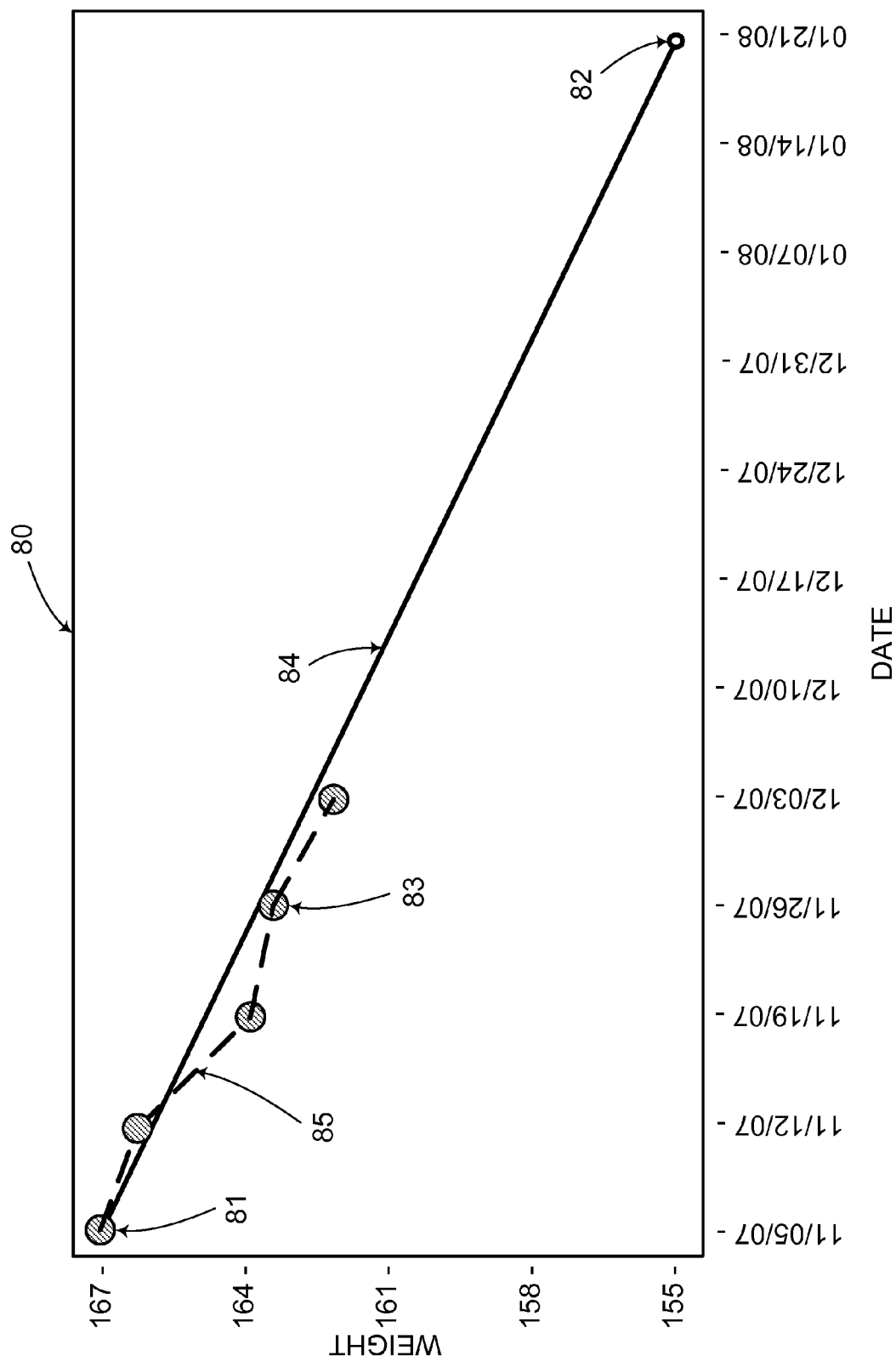
Figure 25:
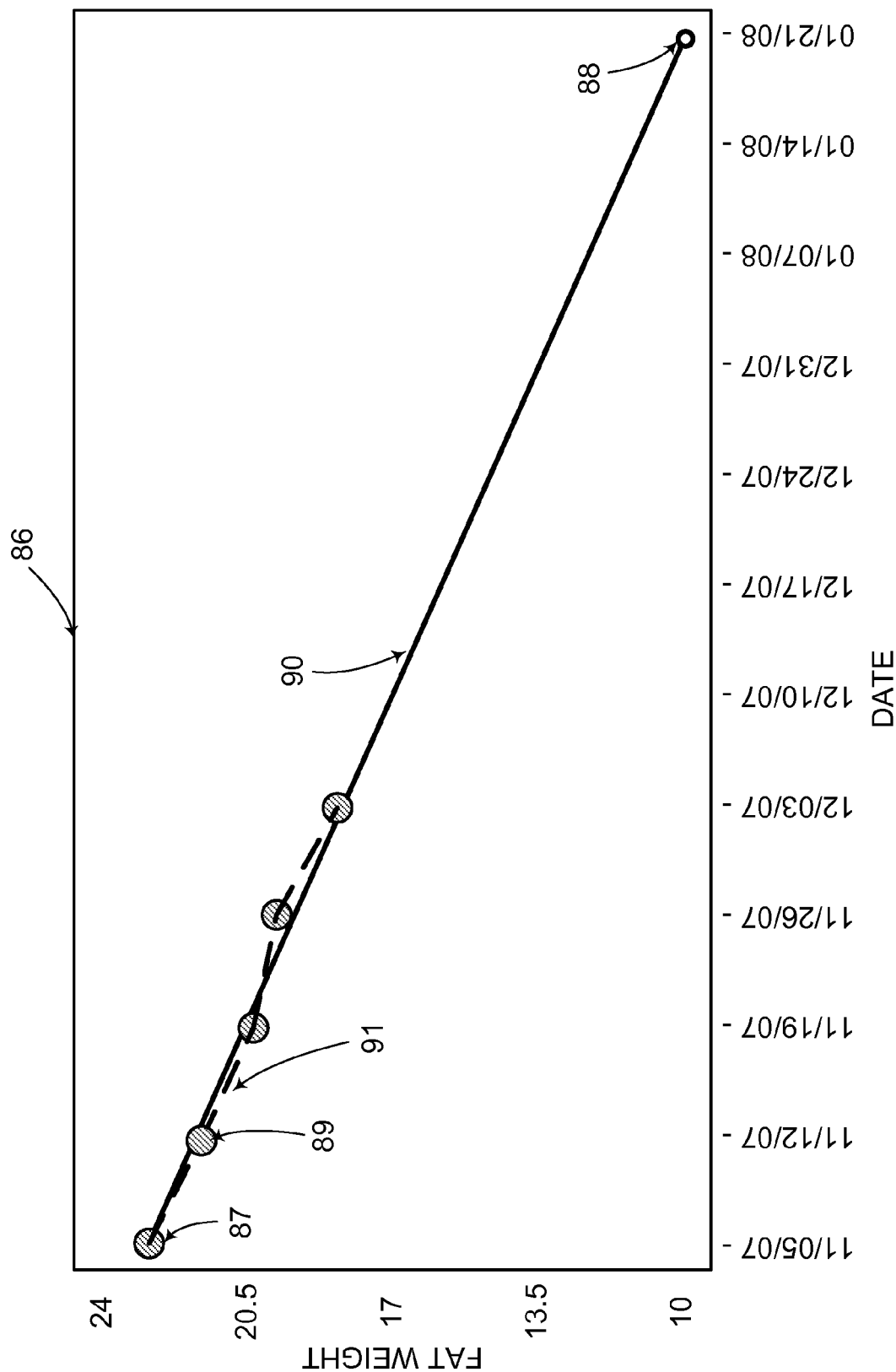
Figure 26:
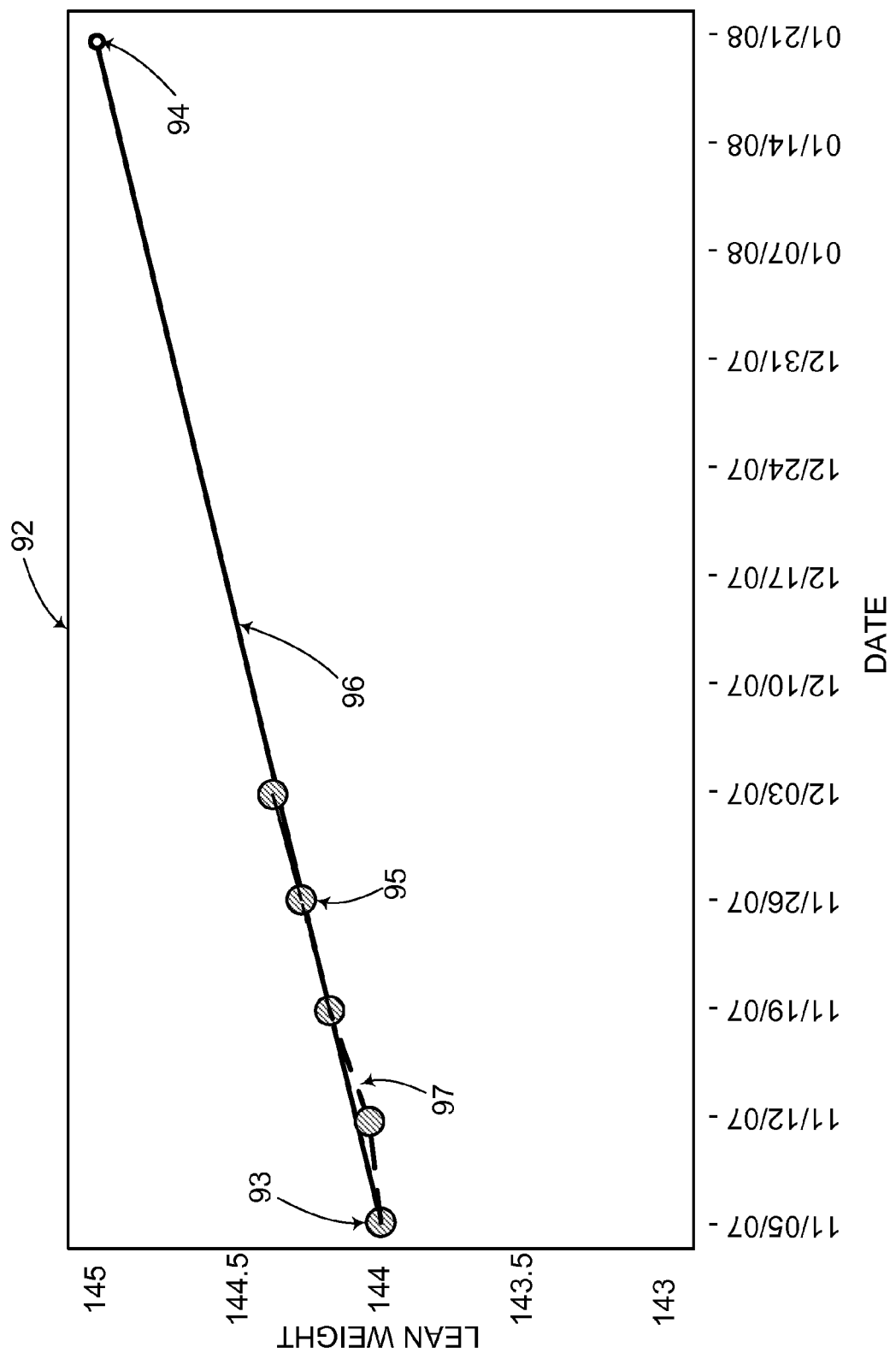

As shown in FIGS. 24, 25, and 26, based on stored actual and goal values (for starting and ending fat weight, lean weight, and composite weight, and the client's base metabolic rate (BMR) derived from body checks), the amount of expected fat loss per day and progressions of lean weight and composite weight that will be produced by a planned program can be calculated. This allows a straight-line graph (which we sometimes call a glide slope) from an upper left starting point to the lower right target finish point, of expected progress, to be produced and used as a foundation for a multi-series graph that plots actual progress over expected progress. On each date when a body check is performed, the resulting point is charted on FIG. 24 together with a path segment. This provides immediate feedback to the client regarding her progress toward personal goals and immediate confirmation that progress is on track or that a goal is in jeopardy. Minor variations from the glide slope will result in messages recommending modification to nutrition, cardiovascular and resistance training plans. Major variations will trigger a recommendation to revisit the goal setting tool. The goal setting tool may be used to adjust nutrition or exercise values to bring goal and reality into synchronization. More frequent body checks provide opportunity for feedback and confirmation of progress. This allows the client and the trainer to make small modifications to keep progress on track and helps maintain motivation.

Figure 27:
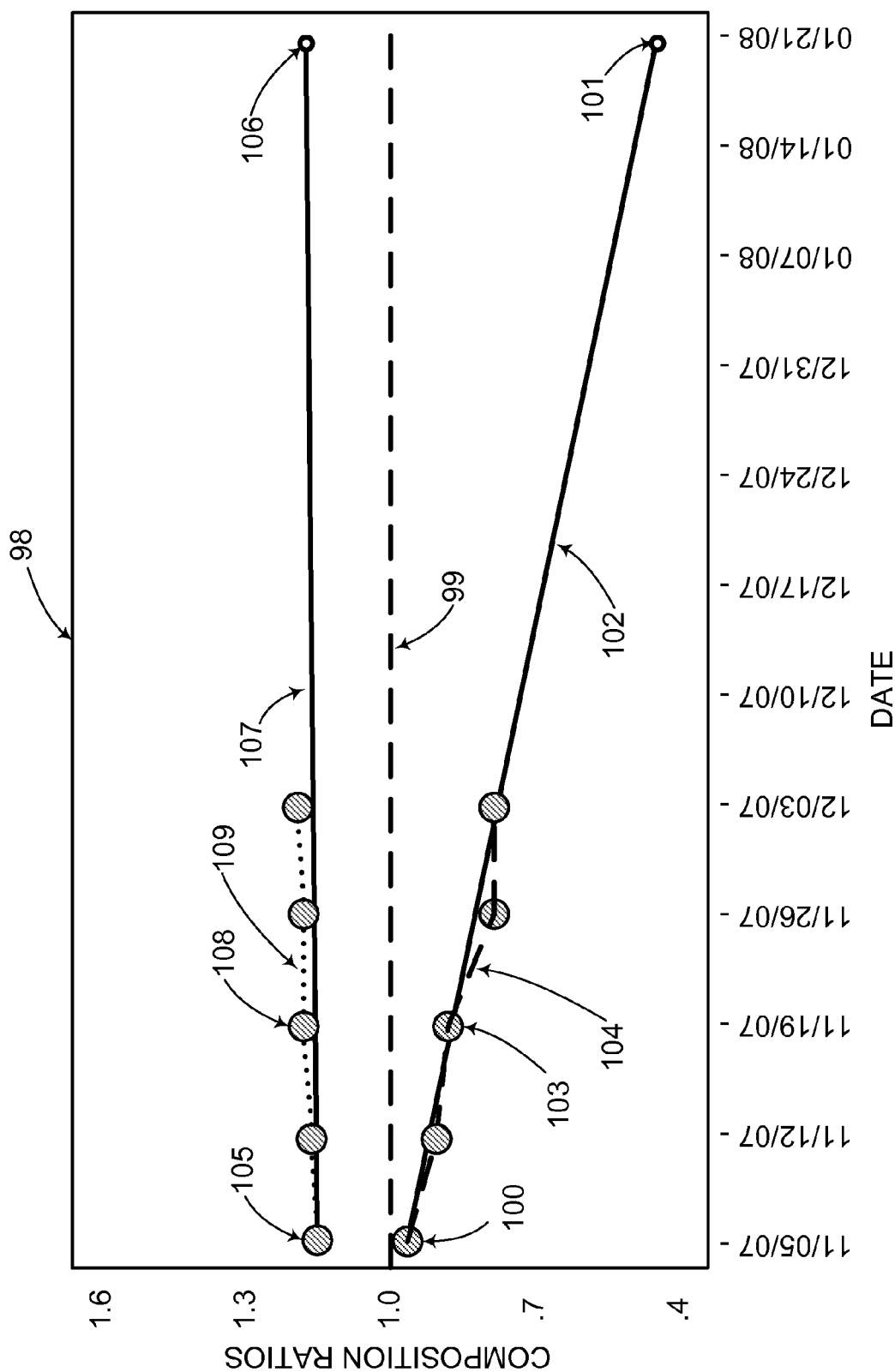

In the example shown in FIG. 24, the vertical scale is of weight, the glide slope represents a linear path of the weight, and the path segments from point to point relate to weight. However, other glide slopes (such as those in FIGS. 25, 26, and 27) can be used either alone or in a suite to show the progression of lean mass ratio, fat mass ratio, and total mass, or other metrics along the vertical axis. All such values or other combinations of values could be illustrated on a single graph. In such an example, a single straight glide slope could represent the anticipated trajectory of all of weight, lean mass ratio, fat mass ratio, and other metrics. Then actual progress on each of the metrics could be illustrated by a separate path. Or different glide slope lines could be shown together with actual trajectories. Or different graphs could be used and displayed independently as illustrated in the figures. In some implementations, the glide slope could be other than a straight line and could represent another desired or feasible trajectory. For example, the trajectory could represent more rapid changes in the value at the beginning and less rapid changes as the target final value is approached.

Figure 28:
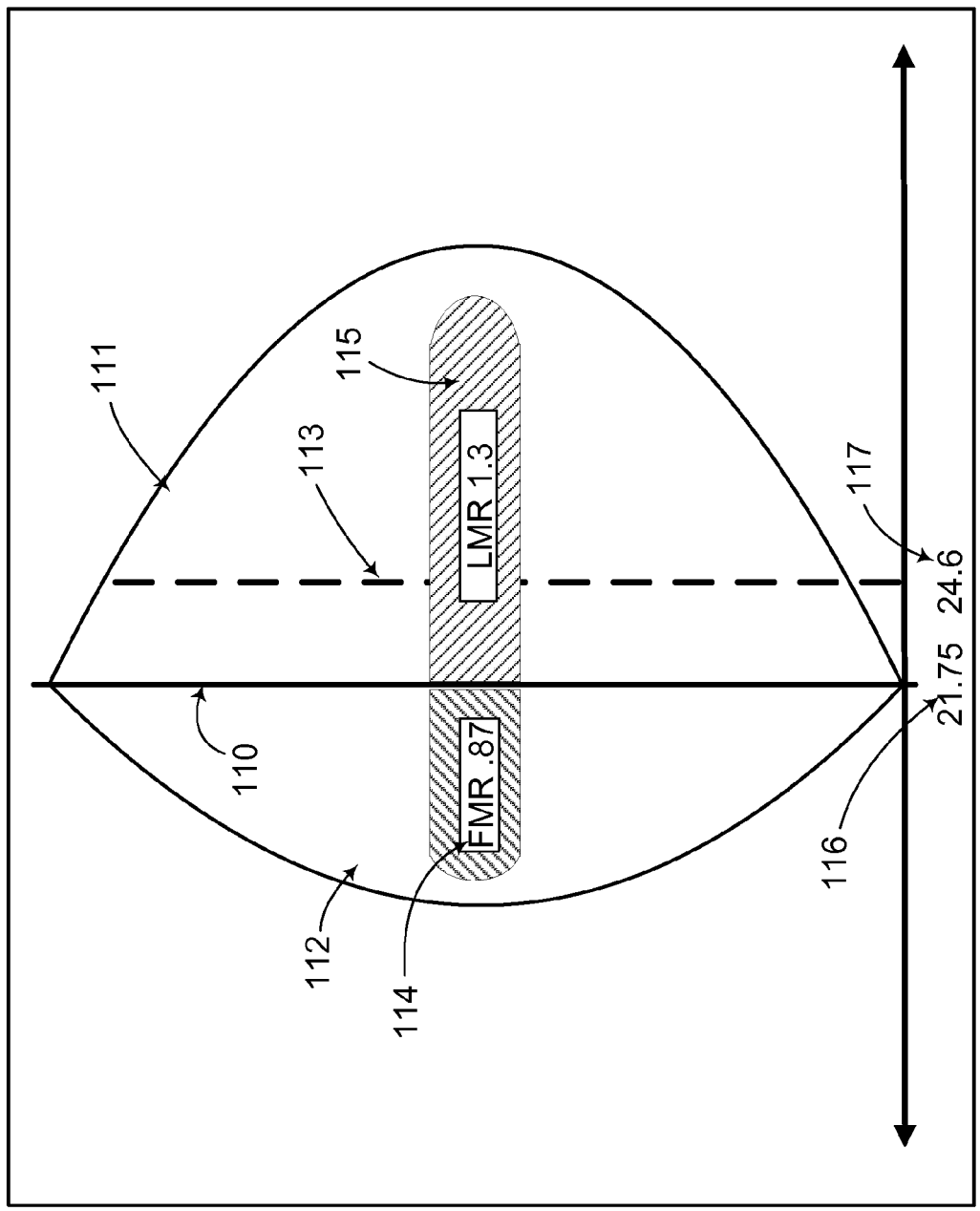

As shown in FIG. 28, another graphical tool that can be displayed to a user to help guide body composition management relates to a factor that we call body mass tension (BMT). One use of BMT is to provide more useful information than is encompassed in a conventional use of BMI. Conventional BMI, which is based only on weight and height, does not track or provide any indication of the contributions of lean body mass (or lean mass ratio) or fat body mass (or fat mass ratio) to the resulting BMI value. For example, a BMI value can be low and seemingly represent a healthy individual, even though the individual actually has insufficient lean mass and excess fat mass. Conversely, an individual who has a high conventional BMI may be quite healthy when viewed in light of the person's relatively high lean body mass.

BMT exposes these inaccuracies of conventional BMI. In FIG. 28, the x axis represents values of BMI. The vertical line 110 at 21.75 indicates that, under a classic view of BMI, a normal BMI 116 for the client is 21.75. Thus, if the client's BMI were to reach 21.75 after a goal session were completed, under this classic view, the client would be in a good state. We refer to 21.75 as the legacy BMI value 116.

The portion of FIG. 28 above the x-axis is a conceptual graphical device that illustrates how the acceptable BMI value for a client can be adjusted using a BMT factor 117 based on the actual or planned composition of the client's body in terms of fat mass ratio and lean (e.g., muscle) mass ratio. The conceptual graphical device comprises the vertical line 110 and two bows 112 and 111 that lie to the left and right of the vertical line. The shapes of the two bows are somewhat arbitrary and are intended to suggest tension that is placed on the vertical line to pull it to the left or right, depending on the fat mass ratio and the lean mass ratio. The fat mass ratio is represented by the length of a bar 114 that has a base lying on the vertical line and a tension-applying end at the left. The lean mass ratio is represented by the length of an opposite bar 115 that has its base on the vertical line and a tension-applying end to the right. The lean mass bar conceptually can pull the ideal BMI value to the right and the fat mass bar conceptually can pull the ideal BMI value to the left. The composite impact of the two bars on BMI is represented by the product of the lean mass ratio and the fat mass ratio. Multiplying the result of that product by the conventional BMI yields the BMT-adjusted BMI value.

If both ratios were 1.0, for example, their product would be 1.0 and applying that factor to the BMI would cause no change in the BMI value.

In a traditional BMI scale, less than 18.5 is considered underweight, between 18.5 and 25 is considered normal, and 21.75 is the mid-point of the normal range and the range extends +/−3.5 points on either side of the mid-point for the normal range. 25 to 30 is considered overweight, 30 to 35 as obese, 35 to 40 as very obese, and more than 40 as very (morbidly) obese.

The adjusted BMI value that results from applying the BMT factor can be viewed as shifting the entire BMI scale in accordance with body composition data for an individual. In the example of FIG. 28, all BMI numbers would be shifted to the right by 2.849 points, which is determined by the formula: BMI shift=((CBMI*(LMR*FMR))−CBMI) (in which CBMI refers to center BMI which is the center value in the normal range in the conventional BMI scale). In the example of FIG. 28, this formula yields ((21.75*(1.3*0.87))−21.75)=2.849.

BMT also can be viewed in a different way, as a factor which is subtracted from the measured actual BMI of a client to correct the value, in this case the corrected value being the calculated BMI of 26.7 (based on measured height and weight) minus the adjustment of 2.849=23.851 (based on body mass composition). This resulting value is in the normal range of the traditional BMI scale. Thus we have corrected the traditional BMI rating of 26.7 (considered overweight) to 23.851 (considered normal).

The client represented in FIG. 28 had an actual BMI of 26.7 (based on weight and height), and might have been told, under a conventional BMI analysis, that she had an increased health risk and an overweight condition relative to a desirable BMI of 21.75. However, the client's LMR was 1.3 and FMR was 0.87 suggesting that a conventional BMI target was not appropriate to her situation. Multiplying the LMR (1.3) by the FMR (0.87) yielded a BMT correction factor of 1.31. When applied to the traditional BMI value of 21.75, the target BMT-corrected BMI value shifted from 21.75 to 24.6, indicating that the client's actual BMI (when adjusted by the factor of 2.849 to 23.851), was acceptable and in the normal range. Illustrating the effect of BMT on BMI helps trainers, health care practitioners, and insurance companies recognize the importance of the relationship between body composition and overall health. A wide variety of other graphical elements and devices could be used to illustrate the impact of lean mass and fat mass on the interpretation of conventional BMI values.

More generally, it is possible to generate a target value for a client based on the person's weight, height, fat body mass, lean body mass, and corresponding physical and demographic characteristics of a population of individuals, which more accurately reflects the desired body mass index taking account of the client's body composition than is the case with the conventional BMI. The generated value can be expressed in terms of an adjustment of a conventional BMI value or in any other useful metric.

Other implementations are within the scope of the following claims.

The invention claimed is:

1. A computer-based method comprising:
   determining a value of maximum fat mass that represents an amount of fat mass that an individual should not exceed for good health, the value of maximum fat mass being determined as a function of height and gender based on a body of statistical data across a population,
   determining a value of minimum lean mass that represents an amount of lean mass that the individual should not fall below for good health, the value of minimum lean mass being determined as a function of height and gender based on a body of statistical data across a population,
   determining quality of the lean mass of the individual,
   enabling the individual or a trainer or health practitioner or dietitian of the individual to manage body composition of the individual based on the determined values of the maximum fat mass and the minimum lean mass, and the quality of the lean mass.

2. The method of claim 1 in which the enabling includes displaying information associated with the determined maximum fat mass and minimum lean mass and measured fat mass and lean mass of the individual to the individual or trainer or health practitioner or dietitian.

3. The method of claim 1 also including
   determining a lean mass ratio and a fat mass ratio from respectively the minimum lean mass value and a measured lean mass, and the maximum fat mass value and a measured fat mass, and
   providing the lean mass ratio and the fat mass ratio to the individual or the trainer or health practitioner or dietitian for use in connection with management of body composition of the individual.

4. The method of claim 1 wherein enabling the individual or the trainer or health practitioner or dietitian to manage body composition of the individual comprises determining quality of the lean mass of the individual.

5. The method of claim 4 wherein the quality comprises strength or stamina.

6. The method of claim 4 wherein determining the quality of the lean mass comprises electromyography measurements.

7. The method of claim 4 wherein determining the quality of the lean mass comprises computing a lean mass ratio.

8. The method of claim 1 further comprising determining a quality of the minimum lean mass that an individual should have.

9. The method of claim 8, wherein the quality comprises strength or stamina.

10. A computer-based method comprising:
receiving demographic, health status, and lean mass, fat mass, and other physical data about a population of individuals,
performing statistical analysis of the received data to establish demographic lean mass and fat mass values across the population, and
making the values that have been established by performing the statistical analysis across the population available to individuals and parties who provide services to individuals in connection with managing body composition, without disclosing the identities or any private information of any of the individuals in the population about whom the data was received.

11. The method of claim 10 in which the physical data is received from the individuals or parties who provide services to the individuals.

12. The method of claim 10 comprising:
deriving a target body composition management value for a person from the person's height, weight, body mass composition, and statistical physical information about a comparable population of individuals, the statistical physical information comprising the lean mass and fat mass values established by performing the statistical analysis across the population, and
providing the target body composition management value for use in managing the person's body composition.

13. The method of claim 12 in which the target body composition management value comprises a body mass index (BMI) value.

14. The method of claim 12 in which the target body composition management value comprises a version of a conventional BMI value that is adjusted based on body composition data.

15. The method of claim 14 in which the conventional BMI value is adjusted upwardly in proportion to a value based on lean body mass and downwardly in proportion to a value based on fat body mass.

16. The method of claim 12 also including displaying information about the target body composition management value to the client or a trainer or health practitioner or dietitian.

17. The method of claim 16 in which the information includes the conventional BMI value and an adjusted BMI value.

18. The method of claim 16 in which the information includes graphical elements illustrating an effect of fat body mass or lean body mass or both on an appropriate BMI value.

19. The method of claim 10 comprising enabling at least two different independent providers of body composition management services to have online access through respective graphical user interfaces to body composition information and plans that are associated with respective clients of the providers and that are stored on the server, the graphical user interfaces being different for different independent providers, at least some of the information and plans associated with the clients of the different independent providers being stored in a common format in a common database maintained by the server.

20. The method of claim 19 in which the providers include trainers or health practitioners or dietitians and entities that employ trainers or health practitioners or dietitians.

* * * * *